(12) United States Patent
Shi et al.

(10) Patent No.: US 11,771,493 B2
(45) Date of Patent: Oct. 3, 2023

(54) TREATMENT APPARATUS FOR ENDOSCOPE, ENDOSCOPE, AND EXPANDABLE FRAME

(71) Applicant: Hangzhou AGS MedTech Co., Ltd., Zhejiang (CN)

(72) Inventors: Baiming Shi, Zhejiang (CN); Peng Li, Zhejiang (CN)

(73) Assignee: Hangzhou AGS MedTech Co., Ltd., Hangzhou (CN)

( * ) Notice: Subject to any disclaimer, the term of this patent is extended or adjusted under 35 U.S.C. 154(b) by 1106 days.

(21) Appl. No.: 16/518,987

(22) Filed: Jul. 23, 2019

(65) Prior Publication Data
US 2019/0357974 A1 Nov. 28, 2019

Related U.S. Application Data

(63) Continuation-in-part of application No. PCT/CN2018/071404, filed on Jan. 4, 2018.

(30) Foreign Application Priority Data

Jan. 23, 2017 (CN) .......................... 201710058825.2

(51) Int. Cl.
*A61B 18/14* (2006.01)
*A61B 90/00* (2016.01)
(Continued)

(52) U.S. Cl.
CPC .......... *A61B 18/1492* (2013.01); *A61B 1/018* (2013.01); *A61B 18/1206* (2013.01);
(Continued)

(58) Field of Classification Search
CPC ........... A61B 2018/00291; A61B 2018/00982; A61B 2018/1495; A61B 2018/1475;
(Continued)

(56) References Cited

U.S. PATENT DOCUMENTS 4,311,143 A * 1/1982 Komiya ............. A61B 18/1442
606/47
2003/0181900 A1 9/2003 Long
(Continued)

FOREIGN PATENT DOCUMENTS

CN 102413786 B 7/2014
CN 104955412 A 9/2015
(Continued)

OTHER PUBLICATIONS

International Search Report of PCT Patent Application No. PCT/CN2018/071404 dated Mar. 29, 2018.
Search report of counterpart European Patent Application No. 18742335.5 dated Feb. 17, 2021.

*Primary Examiner* — Khadijeh A Vahdat
*Assistant Examiner* — Marina Delaney Templeton

(57) ABSTRACT

The present invention provides a treatment apparatus for an endoscope, an endoscope, and an expandable frame. The treatment apparatus for an endoscope includes: a first electrode, including an electrical treatment part and an operating wire; a second electrode, provided inside the endoscope, and including a first electrically conductive part and a sliding contact part electrically connected to the first electrically conductive part, the first electrically conductive part being configured to contact a human body; and a sheath, provided on a surface thereof with a second electrically conductive part, where the operating wire is configured to be passed through the sheath, the sheath is configured to be passed through the endoscope, and when the sheath is located in a preset position, the sliding contact part contacts and is electrically connected to the second electrically conductive part and the sheath is in sliding fit with the sliding contact part.

13 Claims, 33 Drawing Sheets

(51) Int. Cl.
*A61B 1/018* (2006.01)
*A61B 18/12* (2006.01)
*A61B 1/00* (2006.01)
*A61B 18/16* (2006.01)
*A61B 18/00* (2006.01)

(52) U.S. Cl.
CPC ........ *A61B 90/361* (2016.02); *A61B 1/00133* (2013.01); *A61B 1/00135* (2013.01); *A61B 18/16* (2013.01); *A61B 2018/00553* (2013.01); *A61B 2018/00982* (2013.01); *A61B 2018/126* (2013.01); *A61B 2018/1467* (2013.01)

(58) Field of Classification Search
CPC ...... A61B 2018/1467; A61B 2018/141; A61B 2018/1407; A61B 17/320016; A61B 1/018; A61B 1/00089; A61B 1/05; A61B 1/0058; A61B 1/00137; A61B 1/00135; A61B 1/00131; A61B 18/1492; A61B 18/14; A61B 18/1445; A61B 2017/00296; A61B 2017/00867
See application file for complete search history.

(56) References Cited

U.S. PATENT DOCUMENTS

| | | | | |
|---|---|---|---|---|
| 2005/0080411 | A1* | 4/2005 | Ouchi | A61B 18/1492 606/45 |
| 2006/0276784 | A1* | 12/2006 | Miyajima | A61B 18/1492 606/46 |
| 2007/0034211 | A1* | 2/2007 | Hug | A61B 18/042 128/876 |
| 2007/0156185 | A1* | 7/2007 | Swanson | A61B 18/00 607/2 |
| 2014/0188109 | A1 | 7/2014 | McLawhorn et al. | |
| 2014/0275788 | A1 | 9/2014 | McLawhorn | |
| 2015/0351826 | A1* | 12/2015 | Kroeber | A61B 1/00087 600/105 |
| 2016/0338723 | A1 | 11/2016 | Gray et al. | |

FOREIGN PATENT DOCUMENTS

| | | |
|---|---|---|
| CN | 205697995 U | 11/2016 |
| WO | 2011086753 A1 | 7/2011 |
| WO | 2016080093 A1 | 5/2016 |

* cited by examiner

TREATMENT APPARATUS FOR ENDOSCOPE, ENDOSCOPE, AND EXPANDABLE FRAME

CROSS REFERENCE TO RELATED APPLICATIONS

The present application is a Continuation-in-part Application of PCT Application No. PCT/CN2018/071404 filed on Jan. 4, 2018, which claims the benefit of Chinese Patent Application No. 201710058825.2 filed on Jan. 23, 2017. All the above are hereby incorporated by reference.

BACKGROUND

Technical Field

The present invention belongs to the field of medical instruments, and specifically, to a treatment apparatus for an endoscope, an endoscope, and an expandable frame.

Related Art

There are so far known bipolar treatment instruments for an endoscope that are passed through endoscopes to treat living tissue and the like. Some of the bipolar treatment instruments for an endoscope have, for example, a function of supplying a high-frequency current to a treatment instrument to perform treatments such as incision, cauterization, and hemostasis on living tissue.

As an example of such a treatment instrument for an endoscope, a high-frequency incision instrument that uses a polypectomy snare supplied with a high-frequency current to incise living tissue is recorded in Patent CN102413786B. An electric wire, a passive electrode arranged on a periphery of an extending part, living tissue in contact with the passive electrode, the polypectomy snare, and an operating wire are connected to a feeding electrode to form a current loop to excise a polyp. In addition, a bipolar sphincterotome is recorded in Patent CN205697995U and includes a control part, an insulating sheath, and a cutting part. A distal end of the control part is connected to a proximal end of the insulating sheath. The cutting part includes a cutting electrode, a passive electrode, a cutting electrode wiring terminal that may be connected to the cutting electrode, a passive electrode wiring terminal that may be connected to the passive electrode, a cutting electrode conductor connecting the cutting electrode and the cutting electrode wiring terminal, and a passive electrode conductor connecting the passive electrode and the passive electrode wiring terminal. The cutting electrode and the passive electrode are provided on a distal end of the insulating sheath and are respectively connected to the control part through the cutting electrode conductor and the passive electrode conductor.

However, both the foregoing technical solutions can be improved. First, an active electrode (that is, the foregoing high-frequency treatment part and cutting part) does not have an obvious thermal effect, and a cutting speed is relatively slow, resulting in limited clinical application. Second, an area of contact between a passive electrode and tissue is relatively small, and tissue may be burned accidentally. Third, in both the solutions, the passive electrode and the active electrode are relatively close, the two electrodes may contact or a current may flow through tissue fluids between the electrodes to cause a short circuit failure. Fourth, in a surgical instrument for an endoscope, treatment instruments such as electrocoagulation forceps, biopsy forceps, needle knives, and the like in addition to snares and papilla incision knives need to be electrified to perform incision, cauterization, hemostasis, among other work. The passive electrode in the foregoing technical solution has relatively low adaptability.

SUMMARY

Based on this, to overcome the disadvantages in the prior art, the present invention provides a treatment apparatus for an endoscope, an endoscope, and an expandable frame. The structural design is appropriate, the cutting speed is relatively high, the risk of passive electrode burns is relatively low, and adaptability is provided.

The technical solutions of the present invention are as follows:

A treatment apparatus for an endoscope, comprising: a first electrode, comprising an electrical treatment part and an operating wire; a second electrode, configured to be installed on the endoscope, the second electrode comprising a first electrically conductive part and a sliding contact part electrically connected to the first electrically conductive part, and the first electrically conductive part being configured to contact a human body; a sheath, provided on a surface thereof with a second electrically conductive part, wherein the operating wire is passed through the sheath, the sheath is configured to be passed through the endoscope, and when the sheath is located in a preset position, the sliding contact part contacts and is electrically connected to the second electrically conductive part and the sheath is in sliding fit with the sliding contact part.

In one of the embodiments, further comprising an expandable frame, wherein the expandable frame is configured to be sleeved over the endoscope, the first electrically conductive part is provided outside the expandable frame, the first electrically conductive part is provided on the expandable frame, and a distance between a part, being configured to contact a human body, of the first electrically conductive part and an axis of the endoscope is greater than a radius of the endoscope.

In one of the embodiments, wherein a conductive material is provided on a peripheral surface of the expandable frame, and the conductive material forms the first electrically conductive part.

In one of the embodiments, wherein the expandable frame is silicone rubber that contains several conductive particles, and the conductive particles form the first electrically conductive part.

In one of the embodiments, wherein a layer of a conductive material is provided on an outer surface of the sheath, and the conductive material forms the second electrically conductive part.

In one of the embodiments, wherein a first cavity and a second cavity are formed in the sheath, the operating wire is passed through the first cavity, a third electrically conductive part is provided in the second cavity, and the third electrically conductive part is electrically connected to the second electrically conductive part.

In one of the embodiments, wherein the second electrically conductive part surrounds the sheath by one loop in a circumferential direction of the sheath.

In one of the embodiments, wherein the sliding contact part comprises a fifth electrically conductive part and a sixth electrically conductive part, the sixth electrically conductive part is electrically connected to the first electrically conductive part, and the fifth electrically conductive part is electrically connected to the sixth electrically conductive part.

In one of the embodiments, wherein the expandable frame comprises a sleeve and a flexible part or an elastic part connected to the sleeve, the sleeve is configured to be sleeved over the endoscope, and the sliding contact part is fixed on an inner side of the sleeve.

A treatment apparatus for an endoscope, comprising: a first electrode, comprising an electrical treatment part and an operating wire; and a sheath, provided with a second electrically conductive part on an outer surface thereof, and the second electrically conductive part being configured to be electrically connected to a first electrically conductive part on an endoscope, wherein a first cavity and a second cavity are formed in the sheath, the operating wire is passed through the first cavity, a third electrically conductive part is provided in the second cavity, and the third electrically conductive part is electrically connected to the second electrically conductive part.

In one of the embodiments, wherein the second electrically conductive part is provided on an outer surface of the sheath.

In one of the embodiments, wherein a layer of a conductive material is provided on an outer surface of the sheath, and the conductive material forms the second electrically conductive part.

In one of the embodiments, wherein the second electrically conductive part surrounds the sheath by one loop in a circumferential direction of the sheath.

An expandable frame, wherein the expandable frame is configured to be installed on an endoscope, a diameter of a peripheral surface of the expandable frame is greater than a diameter of a peripheral surface of the endoscope, a first electrically conductive part and a sliding contact part electrically connected to the first electrically conductive part are provided on the expandable frame, the first electrically conductive part is provided on a periphery of the expandable frame to contact human body tissue, and the sliding contact part contacts and is electrically connected to a second electrically conductive part of the treatment apparatus for an endoscope in any one of the foregoing embodiments.

In one of the embodiments, wherein a conductive material is provided on the peripheral surface of the expandable frame, and the conductive material forms the second electrically conductive part.

In one of the embodiments, wherein the expandable frame comprises a sleeve and a transparent cover connected to the sleeve, the sleeve is configured to be sleeved over the endoscope, the transparent cover is transparent or translucent, and the transparent cover is configured to allow the endoscope to obtain an image.

In one of the embodiments, wherein the expandable frame comprises a sleeve and a flexible part or an elastic part connected to the sleeve, the sleeve is configured to be sleeved over the endoscope, and the sliding contact part is fixed on an inner side of the expandable frame.

An endoscope, comprising: a first electrically conductive part, provided on an outer surface of an endoscope, the first electrically conductive part being configured to contact a human body, an instrument passage being provided in the endoscope, the instrument passage being configured to be passed through by a treatment apparatus for an endoscope, a fourth electrically conductive part being provided inside the endoscope, and the first electrically conductive part being electrically connected to the fourth electrically conductive part.

In one of the embodiments, further comprising an expandable frame, wherein the expandable frame is installed outside the endoscope, and the first electrically conductive part is provided on the expandable frame.

In one of the embodiments, further comprising a tissue operation mechanism, wherein the first electrically conductive part and the fourth electrically conductive part are provided on the tissue operation mechanism, and the tissue operation mechanism is installed on the expandable frame.

In one of the embodiments, wherein two first electrically conductive parts are provided, one first electrically conductive part is provided on the tissue operation mechanism, the other first electrically conductive part is provided on the expandable frame, and the first electrically conductive part of the tissue operation mechanism is electrically connected to the first electrically conductive part of the expandable frame. In one of the embodiments, wherein a layer of a conductive material is provided on a peripheral surface of the endoscope, and the conductive material forms the first electrically conductive part.

In one of the embodiments, wherein a connecting through hole is formed in the endoscope, the peripheral surface of the endoscope and the instrument passage are communicated through the connecting through hole, and the conductive material is provided in the connecting through hole to electrically connect the first electrically conductive part to the fourth electrically conductive part.

In one of the embodiments, wherein the conductive material is provided on an end surface at a distal end of the endoscope to electrically connect the first electrically conductive part to the fourth electrically conductive part.

In one of the embodiments, further comprising a tissue operation mechanism, wherein the first electrically conductive part and the fourth electrically conductive part are provided on the tissue operation mechanism.

An expandable frame, configured to be installed outside an endoscope, a first electrically conductive part and a fourth electrically conductive part electrically connected to the first electrically conductive part being provided on the expandable frame, the first electrically conductive part being configured to contact a human body, and the fourth electrically conductive part being configured to be electrically connected to a feeding electrode.

In one of the embodiments, wherein the fourth electrically conductive part is a conductor wire, and the fourth electrically conductive part is configured to be passed through the endoscope or provided outside the endoscope.

The beneficial effects of the present invention are as follows:

The first electrode performs an electrical operation on a human body, and a current that enters the human body is looped through the second electrically conductive part instead of flowing all over the human body, so as to avoid damage to other organs or electronic apparatuses (for example, a pacemaker) in the human body, thereby ensuring the safety of the entire operation. Provided that electrical requirements can be satisfied, the second electrode may be provided at any position in the endoscope, so that a sufficiently large area of contact between the second electrically conductive part and the human body is ensured to fully guide out a current. A space of contact between an outer side of the endoscope body of the endoscope and tissue is fully used to increase a conductive area of a contact part through which a current is guided out from human body tissue in a return path, so that while the risk of burns is reduced, a thermal effect is further improved, thereby improving the security and operation efficiency of endoscopic surgery, and ensuring further clinical popularization and application of the treatment apparatus for an endoscope.

REFERENCE NUMERALS

Figure 1A:
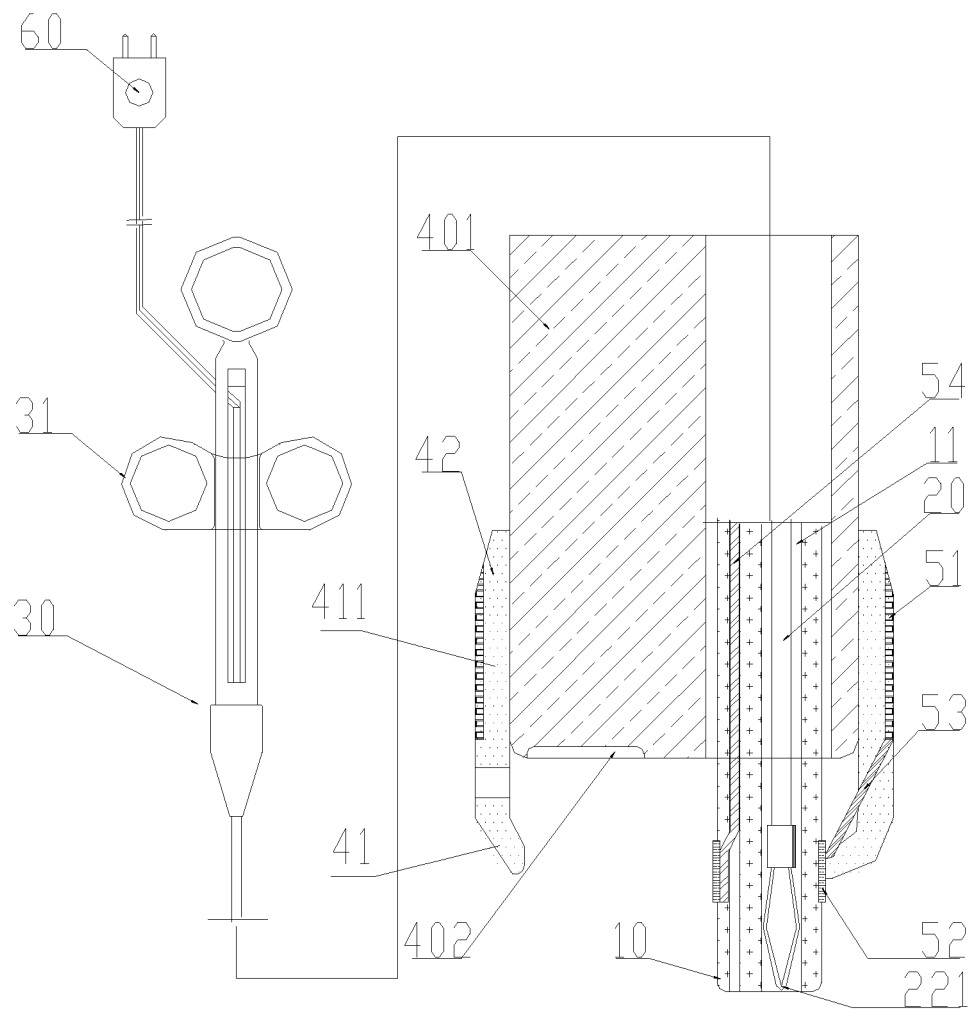
FIG. 1A is a schematic diagram of coordination between a treatment apparatus for an endoscope according to Embodiment 1 of the present invention and an endoscope.

Sheath 10, first cavity 11, second cavity 12, operating wire 20, cutting part 21, ESD knife 222, electric snare 221, electrocoagulation forceps 223, electric biopsy forceps 224, conductor cavity 2251, cutting wire 2252, anchor 2253, drive part 30, sliding ring 31, endoscope body 401, instrument passage 403, transparent cover 41, expandable frame 42, return path 50, first electrically conductive part 51, second electrically conductive part 52, sliding contact part 53, third electrically conductive part 54, fourth electrically conductive part 55, feeding electrode 60, passive electrode 61, active electrode 62, tissue operation mechanism 70.

DETAILED DESCRIPTION

The present invention is further described below in detail, but the implementations of the present invention are not limited thereto.

Embodiment 1

As shown in FIG. 1A to FIG. 3, a treatment apparatus for an endoscope includes: a first electrode, including an electrical treatment part and an operating wire 20; a second electrode, configured to be provided inside the endoscope (not shown), and including a first electrically conductive part 51 and a sliding contact part 53 electrically connected to the first electrically conductive part 51, the first electrically conductive part 51 being configured to contact a human body; and a sheath 10, provided on a surface thereof with a second electrically conductive part 52, where the operating wire 20 is passed through the sheath 10, the sheath 10 is passed through the endoscope, and the sheath 10 is movable back and forth in an instrument passage of the endoscope. Specifically, the sheath 10 of the present invention is passed through the instrument passage 403 of the endoscope and is controlled by a drive part 30 (a sliding ring 31 is provided on the drive part 30) connected outside a body to move freely forward or backward in the instrument passage 403.

Figure 2:
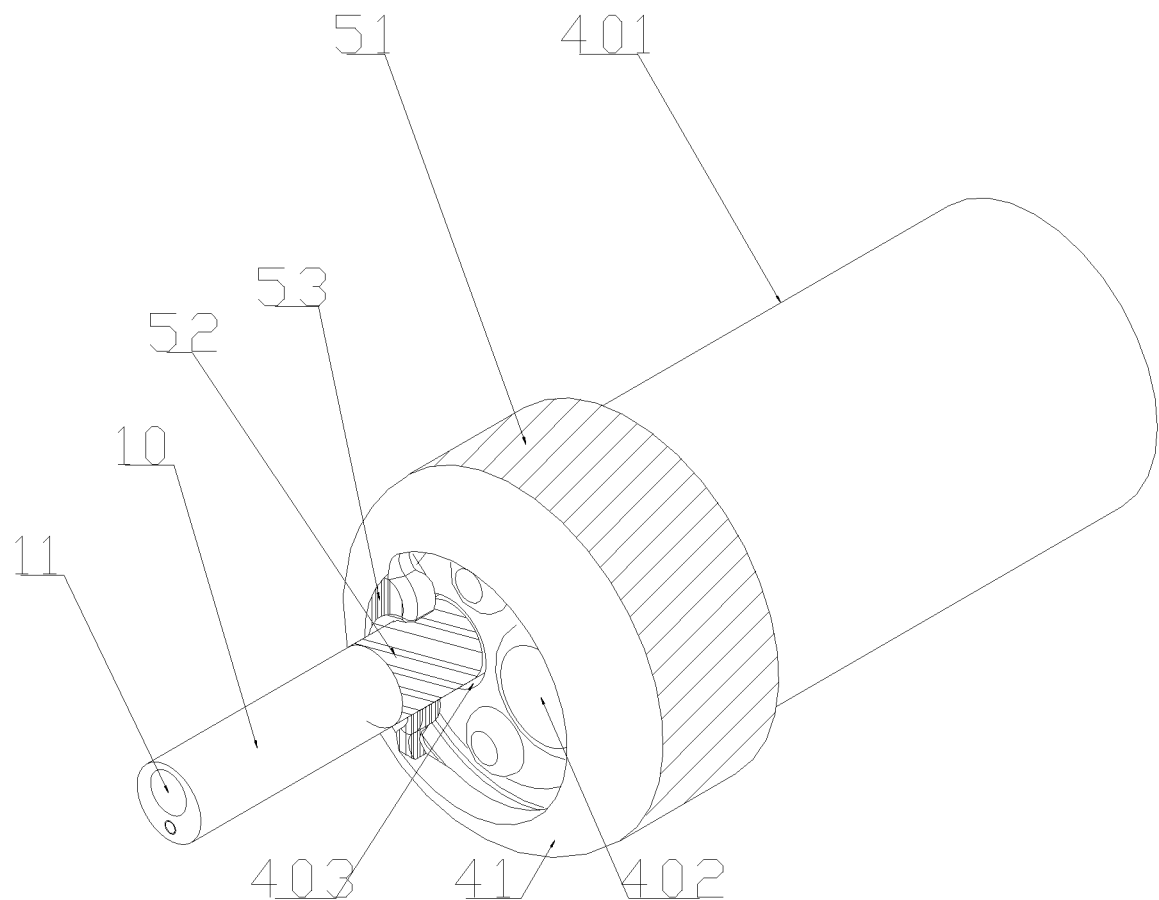
FIG. 2 is a schematic diagram of an expandable frame installed in a treatment apparatus for an endoscope according to Embodiment 1 of the present invention.

As shown in FIG. 2, a first cavity 11 extending in an axial direction and having openings at two ends is formed in the sheath 10. The sheath 10 is made of an insulating material, for example, insulating resin. In addition, preferably, the sheath 10 needs to be flexible enough to bend and move forward or backward along lumen tissue and the like in an organism.

Figure 1B:
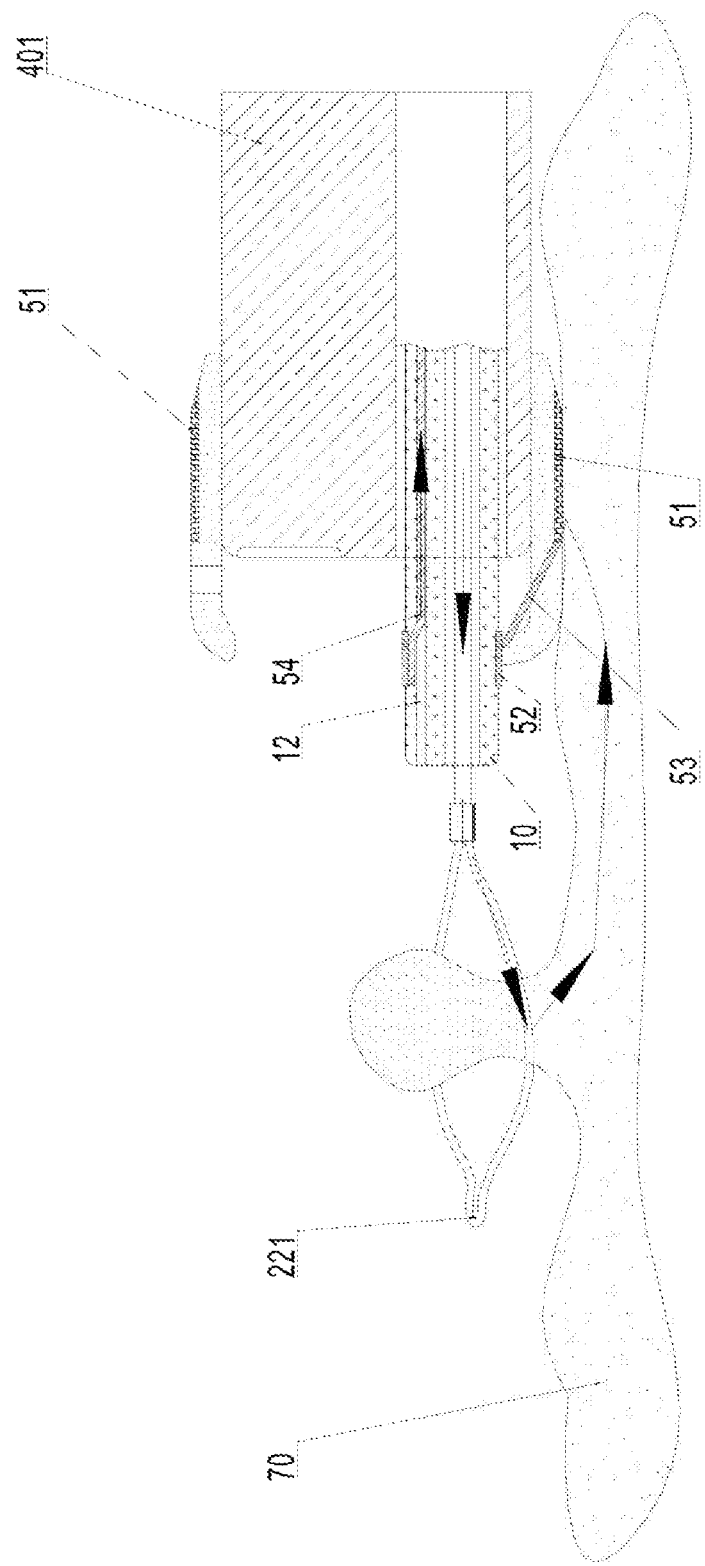
FIG. 1B is a schematic diagram of coordination between a treatment apparatus for an endoscope according to Embodiment 1 of the present invention and an endoscope.
Figure 4:
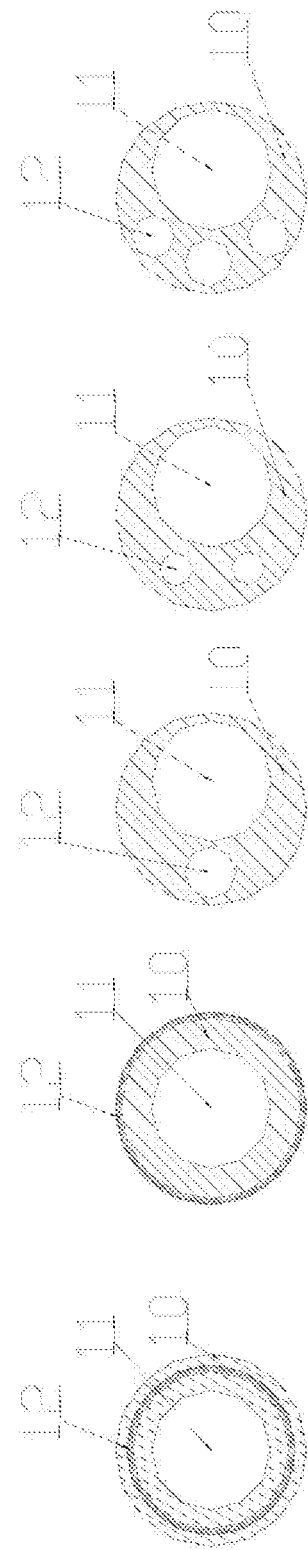
FIG. 4 is a diagram showing several arrangement manners of a second conductive body according to Embodiment 1 of the present invention.

As shown in FIG. 1A, FIG. 1B, and FIG. 4, the first cavity 11 and a second cavity 12 are formed in the sheath 10. The conductive operating wire 20 is passed through the first cavity 11 in a manner of moving freely forward or backward. The electrical treatment part (including, but not limited to, an endoscopic submucosal dissection (ESD) knife 222, an electric snare 221, electrocoagulation forceps 223, electric biopsy forceps 224, and a papilla sphincterotomy hereinafter) is provided at a distal end of the operating wire 20, and in this embodiment, is an electric snare. The operating wire 20 is conductive. A proximal end of the operating wire 20 is electrically connected to an active electrode 62 of a feeding electrode 60 (in the present invention, the feeding electrode 60 includes a passive electrode 61 and the active electrode 62, referring to FIG. 14 for details). Although the operating wire 20 is conductive (or even the operating wire 20 and the electrical treatment part may be one overall conductor) in this embodiment, the specific material and performance of the operating wire 20 are not limited, provided that the electrical treatment part can be manipulated to move forward or backward. Alternatively, the operating wire 20 may be not conductive, and a conductor wire is additionally used between the electrical treatment part and an electrode to establish a conductive connection.

Figure 3:
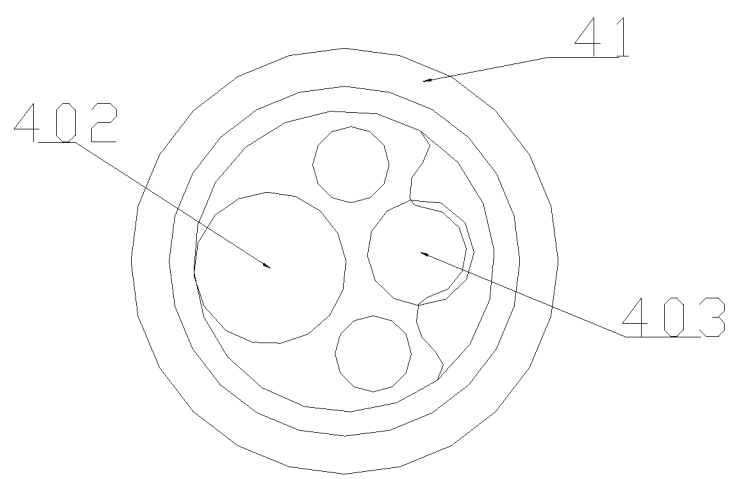
FIG. 3 is a schematic diagram of an end surface in FIG. 2.

An expandable frame is sleeved over a front end of the endoscope. As shown in FIG. 2 and FIG. 3. The expandable frame 42 includes a sleeve 411 sleeved over the endoscope and a transparent cover 41. The transparent cover 41 is made of a transparent insulating material. The transparent cover 41 may block a part of the view of a camera 402 (as shown in FIG. 1 and FIG. 2) of the endoscope, and the endoscope may obtain an image through the transparent cover 41. The first electrically conductive part 51 is provided on a periphery of the expandable frame. A diameter of a peripheral surface of the expandable frame is greater than a diameter of a peripheral surface of the endoscope. The sliding contact part 53 may be provided on the expandable frame.

Figure 5A:
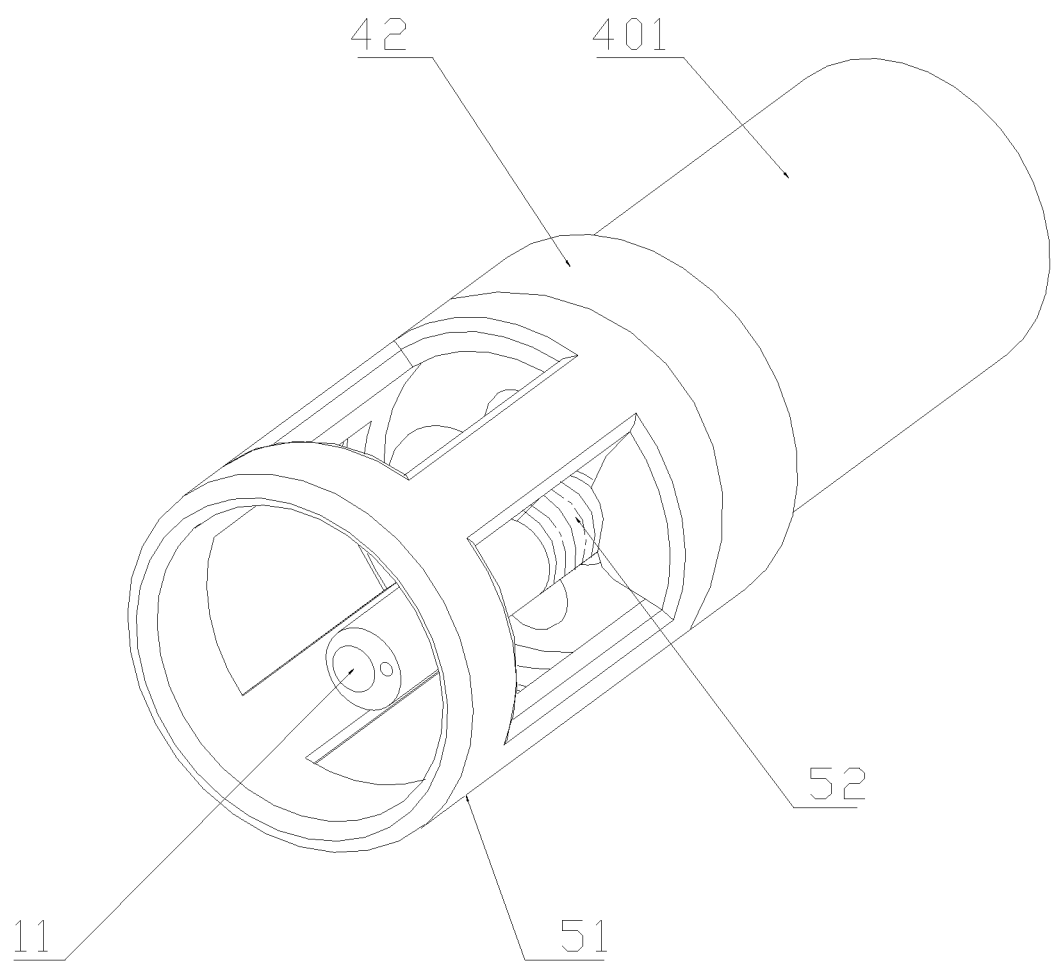
FIG. 5A to FIG. 5C are schematic diagrams of other implementations of the expandable frame according to Embodiment 1 of the present invention and an endoscope.
Figure 5B:
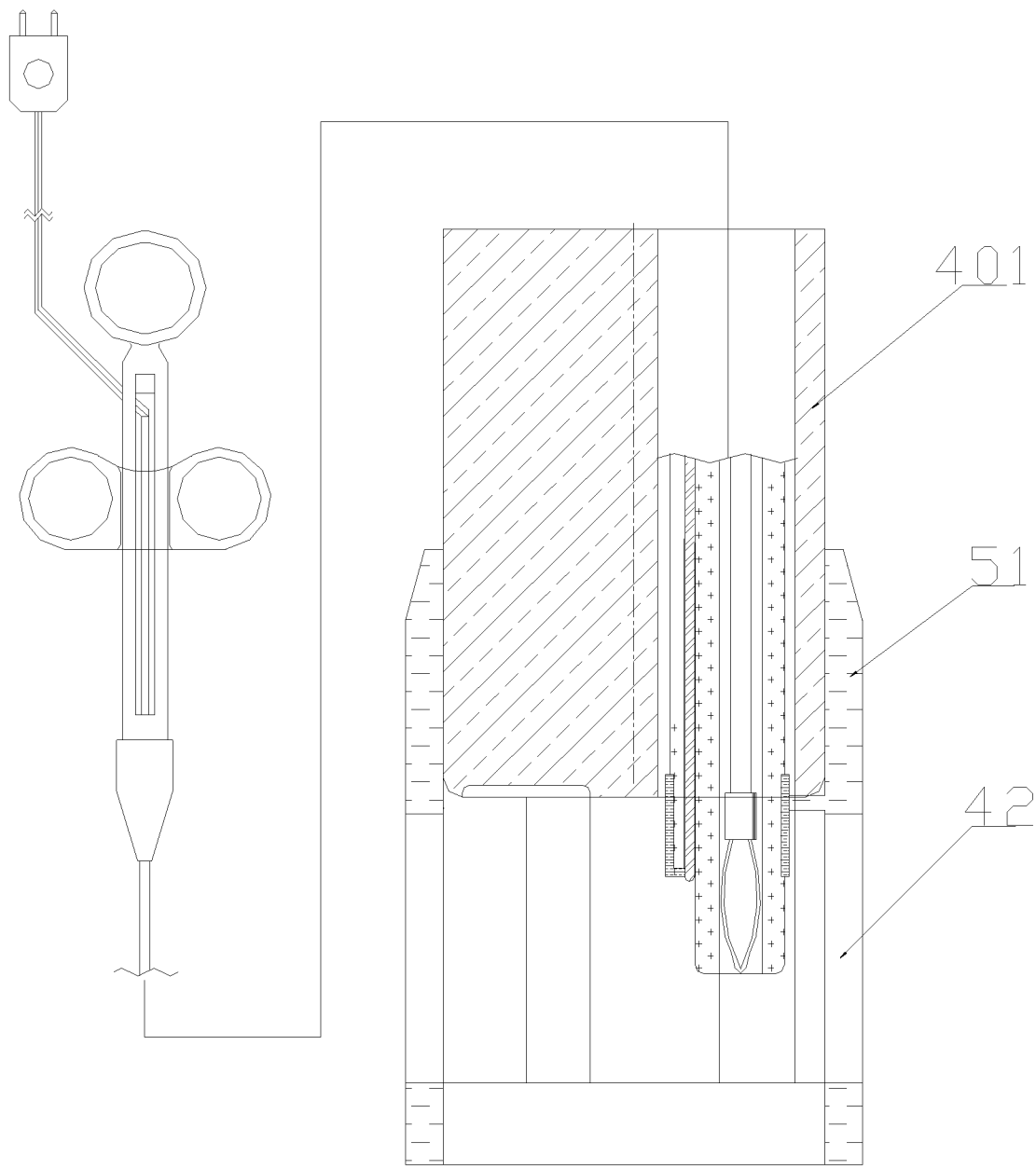
Figure 5C:
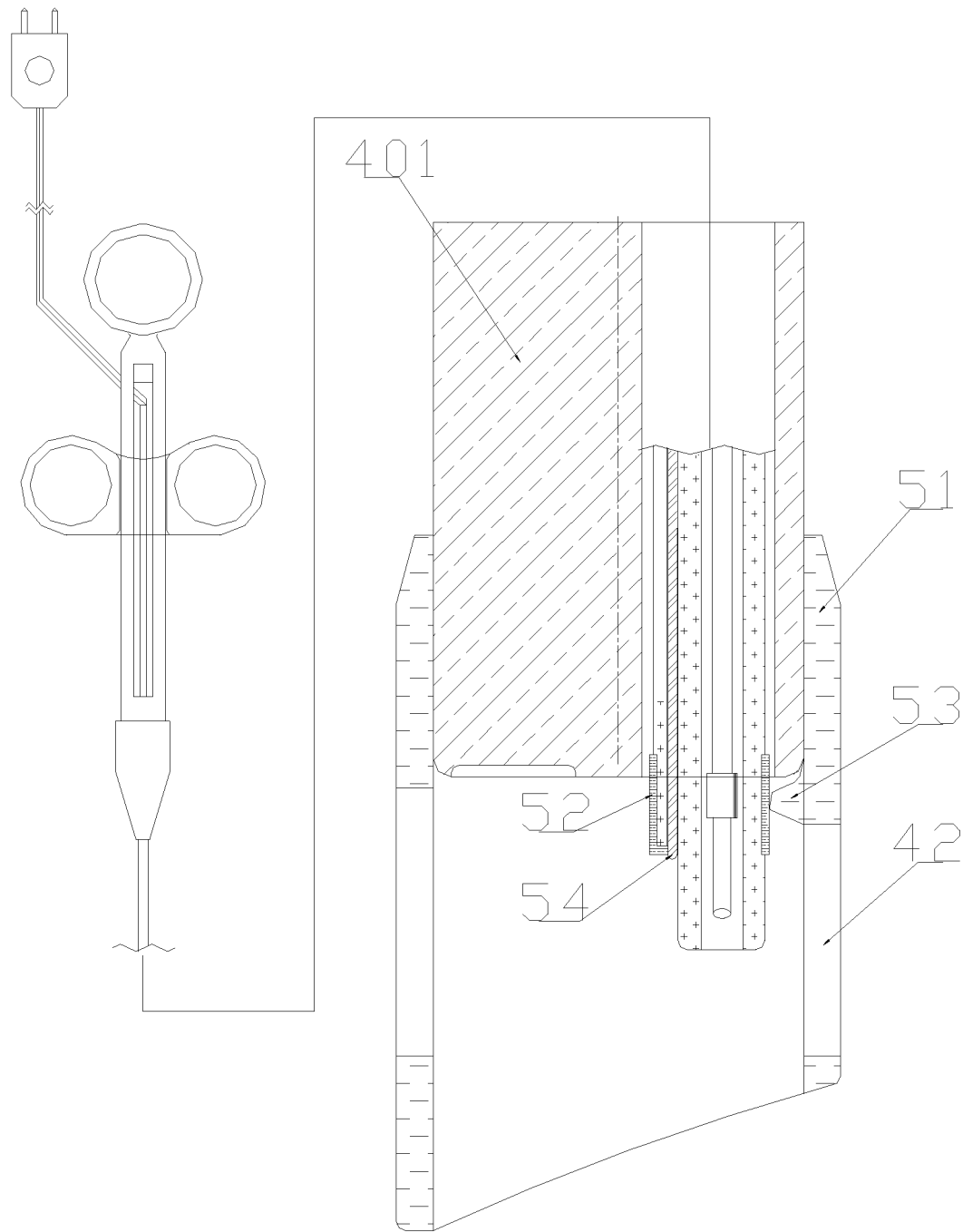

FIG. 5A, FIG. 5B, and FIG. 5C further show other implementations in which the expandable frame 42 is installed on the treatment apparatus for an endoscope. During use, the expandable frame 42 is assembled at a distal end of an endoscope body 401 of the endoscope, the first electrically conductive part 51 is provided on a periphery of the expandable frame, and the first electrically conductive part 51 has a relatively large surface area to fully contact human body tissue. Preferably, a structure of the first electrically conductive part 51 may be as follows: A conductive material is provided on a peripheral surface of the endoscope 42, and the conductive material forms the first electrically conductive part 51. The type of the conductive material may be selected as required. In addition, preferably, the sliding contact part 53 is provided on the expandable frame 42 and has conductive performance A part of the sliding contact part 53 is electrically connected to the first electrically conductive part 51, and another part of the sliding contact part 53 forms tight fit with a periphery of the sheath and is electrically connected to the second electrically conductive part 52.

Figure 7A:
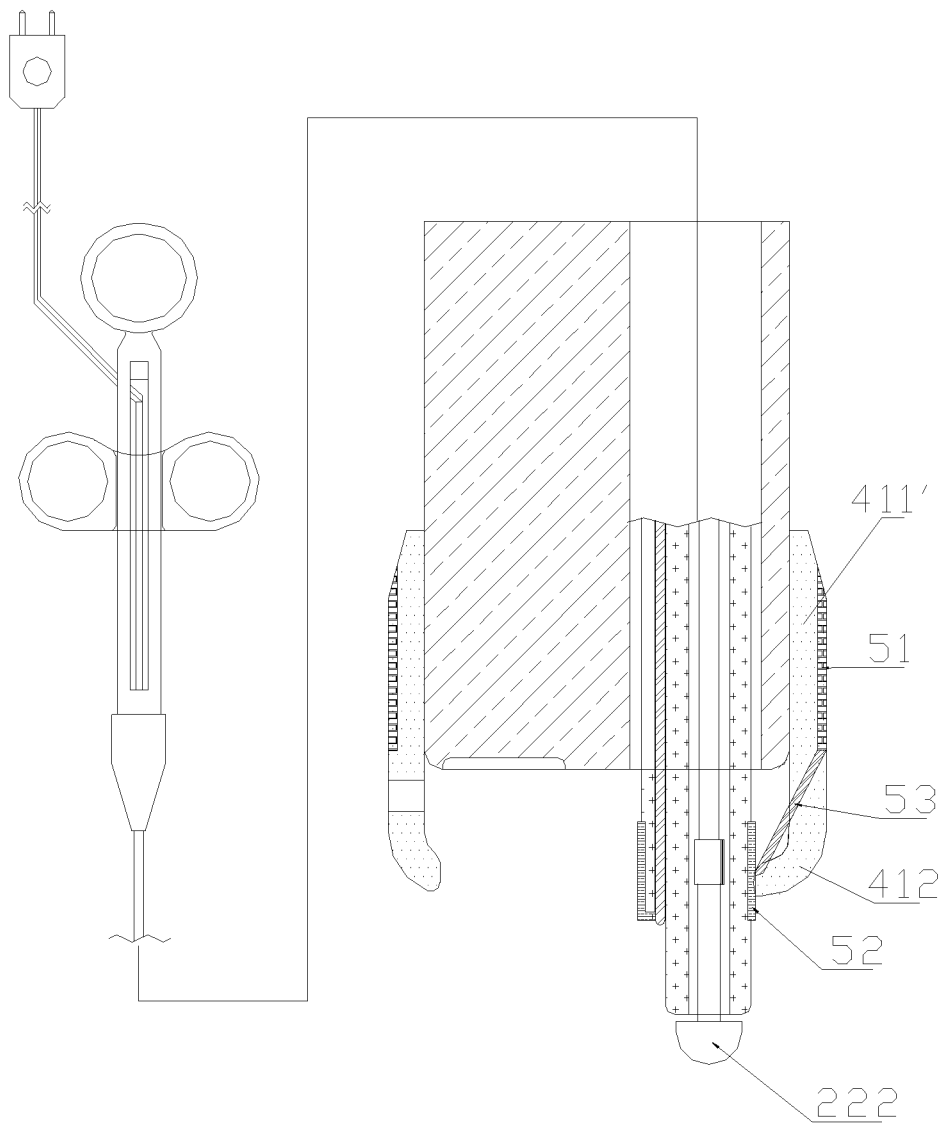
FIG. 7A to FIG. 13 are schematic diagrams according to another implementation of the present invention.

It should be noted that although the expandable frame 42 with a transparent cap 41 is provided in the foregoing embodiment, the foregoing two structures are not limited, provided that is an auxiliary apparatus for an endoscope can be tightly attached to a side wall of tissue and has a larger surface area than the sheath, so that the first electrically conductive part 51 may be attached to the peripheral surface of the peripheral surface of the expandable frame 42 and is connected to the second electrically conductive part 52 through the sliding contact part 53 to achieve the same effect. Preferably, as shown in FIG. 7A, the expandable frame 42 includes a sleeve 411' and a flexible part or an elastic part 412 connected to the sleeve 411', the sleeve 411' is configured to be sleeved over the endoscope, and the sliding contact part 53 is fixed on an inner side of the expandable frame or an inner side of the sleeve 411'. The flexible part or elastic part 412 provides particular cushioning for the sliding contact part 53 or applies particular pressure to keep electrical contact between the sliding contact part 53 and the second electrically conductive part 52, so that the sliding contact part 53 is kept being configured to be electrically connected to the second electrically conductive part 52.

Further, as shown in FIG. 2 and FIG. 3, the second electrically conductive part 52 is fixed at a position, at a distance of L1 near a top end, on a periphery of a front section of the sheath 10, and is conductive. An outer diameter of the second electrically conductive part 52 does not exceed an inner diameter of the instrument passage 403. Moreover, referring to both FIG. 1B and FIG. 4, the second cavity 12 is formed in the sheath 10. A third electrically conductive part 54 having a conductive function is encapsulated in the second cavity 12. The second electrically conductive part 52 is electrically connected to the third electrically conductive part 54, and the second electrically conductive part 52 is electrically connected to a passive electrode 61 of the feeding electrode 60 through the third electrically conductive part 54, and an external power supply supplies power to the electric snare. The present invention is not limited thereto. Alternatively, a layer of a conductive material is provided on an outer surface of the sheath 10, and the conductive material forms the second electrically conductive part 52. The type of the conductive material may be selected as required. The layer of the conductive material at least covers a peripheral surface of a part of the sheath 10. The layer of the conductive material may be made very thin to reduce an increase in an additional volume. Preferably, the layer of the conductive material is made smooth to facilitate the movement of the sheath 10 in the instrument passage of the endoscope.

Although the third electrically conductive part 54 is encapsulated in the sheath 12 in this embodiment, a specific position of the third electrically conductive part 54 on the sheath is not limited, provided that the third electrically conductive part 54 is electrically isolated from the electric snare 221 in the first cavity 11 and is eventually electrically connected to the first electrically conductive part 51. FIG. 4 shows several arrangement manners of the third electrically conductive part 54 in the sheath 12.

Although the third electrically conductive part 54 has a linear shape in this embodiment, the specific shape and structure of the third electrically conductive part 54 are not limited, provided that the third electrically conductive part 54 can electrically connect the first electrically conductive part 51 to the feeding electrode and can bend in accordance with a flexible cavity.

Figure 12:
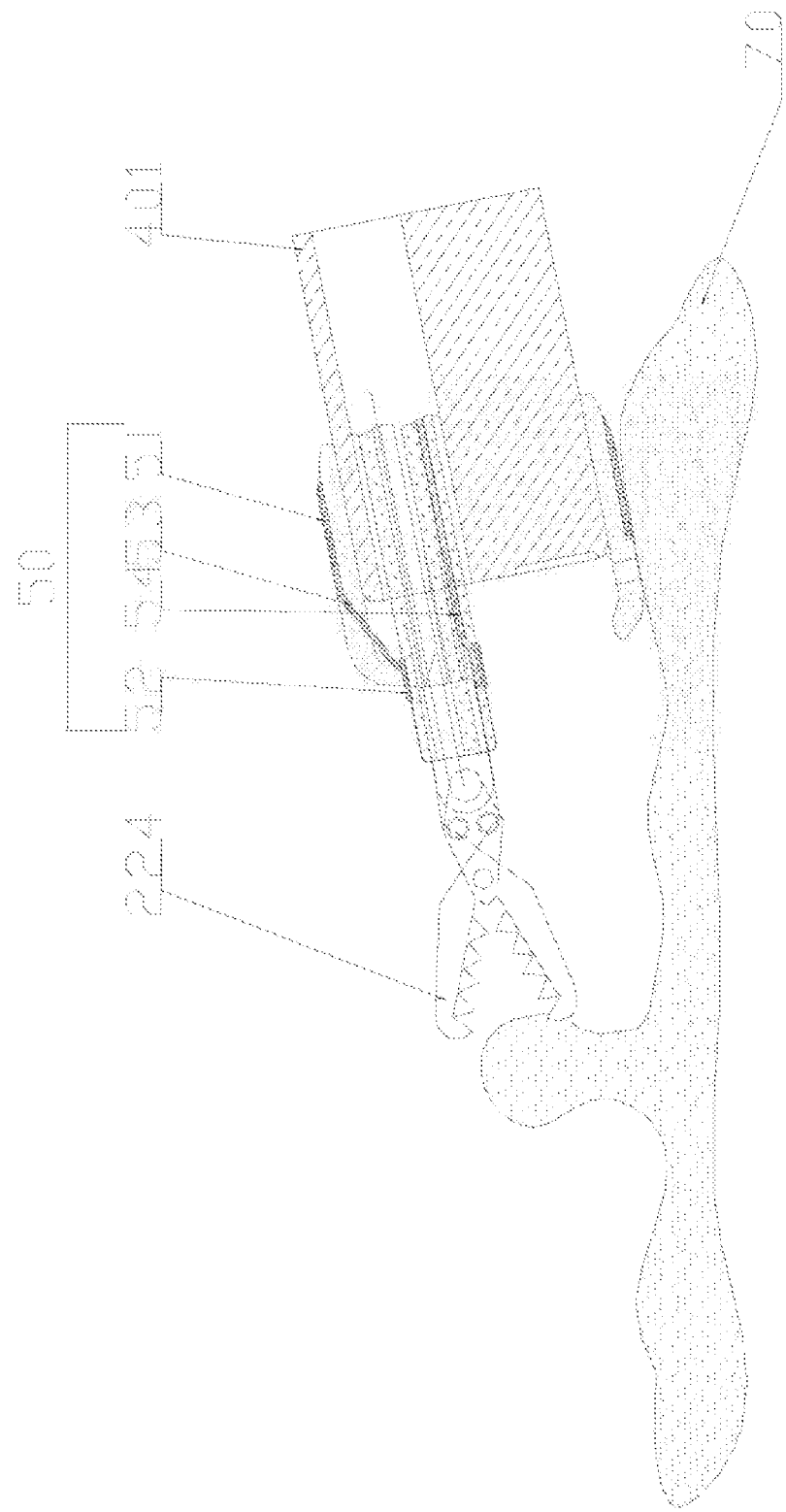

A working manner of the present invention is described below. Before operations of endoscopic surgery are started, the expandable frame 42 with the first electrically conductive part 51 is assembled at a distal end of an endoscope body 401 of the endoscope, and the sheath 10 with the electric snare 221 is further inserted in the instrument passage 403 of the endoscope. Next, the endoscope is inserted in a cavity (for example, a digestive tract, a vagina) of a human body, and an image transmitted by the camera 402 is simultaneously observed. When a focus is reached, a sliding ring 31 on the drive part 30 is operated, the electric snare 221 is closed around tissue to be excised, and the first electrically conductive part 51 is tightly attached to tissue 70 on a side wall at the same time. Finally, the feeding electrode 60 is turned on, and a current flows through the active electrode 62 of the feeding electrode 60, the electric snare 221, the tissue to be excised, and a return path 50 (as shown in FIG. 12, the return path 50 includes the first electrically conductive part 51, the sliding contact part 53, the second electrically conductive part 52, and the third electrically conductive part 54), and returns to the passive electrode 61 of the feeding electrode 60 to form a loop. High heat is generated at a contact position between the electric snare 221 and the tissue to be excised to excise the tissue. For the formation of the return path 50, and when the sheath 10 is located in a preset position, the sliding contact part 53 contacts and is electrically connected to the second electrically conductive part 52 and the sheath 10 is in sliding fit with the sliding contact part 53. The preset position is not necessarily a point, and it may be designed that when the sheath 10 slides within a particular range, the sliding contact part 53 can contact and be electrically connected to the second electrically conductive part 52. In this way, the first electrically conductive part 51, the sliding contact part 53, the second electrically conductive part 52, and the third electrically conductive part 54 form the return path 50 of the current guided out from the human body. In a conventional instrument for an endoscope, the return path 50 is not provided or no other manner is used to guide out a current, and a reliable electrical connection to the human body cannot be kept as well as in the present invention, easily resulting in accidental injury. Because the first electrically conductive part 51 is close to the electrical treatment part, a current that enters the human body is guided out by the first electrically conductive part 51 instead of flowing all over the human body. Therefore, a stronger current can be used, so as to obtain electrothermal efficiency that cannot be obtained by a conventional electric snare 221, and the stronger current generates more heat at the focus. The description of the active electrode 62 and the passive electrodes 61 herein and in the context is only used for ease of recognizing a current direction in a same loop, and an actual flowing direction of a current is not limited. A high-frequency alternating current with a frequency not less than 20 KHZ usually flows in the formed loop.

It should be noted that the foregoing electrical contact and electrical connection means that a current can be in practice conducted. For such contact, two entities may contact or the entities may not contact (there is a gap) but complete conduction of a current by means of conductive liquids (for example, tissue fluids, and secretions) in a human body.

The preferred solutions and beneficial effects of this embodiment are as follows:

1. The treatment apparatus for the endoscope includes: the first electrode, including the electrical treatment part and the operating wire 20, where the electrical treatment part is configured to perform an electrical operation on a human body, and the electrical operation includes, but is not limited to, an electric shock effect, an electric heating effect, and an electrical cauterization effect; the second electrode, configured to be installed inside the endoscope, and including the first electrically conductive part 51 and the sliding contact part 53 electrically connected to the first electrically conductive part 51, and the first electrically conductive part 51 being configured to contact a human body; and the sheath 10, the second electrically conductive part 52 being provided on the surface of the sheath 10, where the operating wire 20 is passed through the sheath 10, the sheath 10 is passed through the endoscope, the sheath 10 is movable back and forth in the instrument passage of the endoscope, and when the sheath 10 is located in a preset position, the sliding contact part 53 contacts and is electrically connected to the second electrically conductive part 52 and the sheath 10 is in sliding fit with the sliding contact part 53.

The first electrode performs an electrical operation on a human body, and a current that enters the human body is looped through the second electrically conductive part instead of flowing all over the human body, so as to avoid damage to other organs or electronic apparatuses (for example, a pacemaker) in the human body, thereby ensuring the safety of the entire operation. Provided that electrical requirements can be satisfied, the second electrode may be provided at any position in the endoscope, so that a sufficiently large area of contact between the second electrically conductive part 52 and the human body is ensured to fully guide out a current.

2. The treatment apparatus for the endoscope further includes the expandable frame 42. The expandable frame 42 is configured to be sleeved over the endoscope. The first electrically conductive part 51 is provided on a periphery of the expandable frame 42. A distance between a part, being configured to contact a human body, of the first electrically conductive part 51 and an axis of the endoscope is greater than a radius of the endoscope. The expandable frame 42 is used to increase the distance between the part, being configured to contact the human body, of the first electrically conductive part 51 and the axis of the endoscope. Because the sheath 10 is passed through the endoscope, the first electrically conductive part 51 contacts the human body first, thereby ensuring reliable contact between the first electrically conductive part 51 and the human body and avoiding electrical leakage.

Provided that electrical requirements can be satisfied, the expandable frame 42 may be provided at any position of the endoscope. Preferably, the expandable frame is provided at a distal end of the endoscope, and the expandable frame is kept as close as possible to the electrical treatment part of the first electrode, thereby reducing a path of a current flowing through the human body.

3. A conductive material is provided on the peripheral surface of the expandable frame 42, and the conductive material forms the first electrically conductive part 51. The type of the conductive material may be selected as required. The layer of the conductive material at least covers a peripheral surface of a part of the expandable frame 42. The layer of the conductive material may be made very thin to reduce an increase in an additional volume. Preferably, the layer of the conductive material is made smooth to reduce damage to the human body. In this embodiment, the expandable frame has a cylindrical shape, but is not limited thereto. Another shape may be used, provided that the expandable frame can be installed inside the endoscope.

4. The expandable frame 42 includes a sleeve and a transparent cover connected to the sleeve. The sleeve is configured to be sleeved over the endoscope. The transparent cover is transparent or translucent. The transparent cover is configured to allow the endoscope to obtain an image. When a part, blocking an optical device (including, but is not limited to, a camera, a lighting device) of the endoscope, of the cover of the expandable frame 42 is made transparent or translucent, it is ensured that the optical device acquires an image normally.

5. The expandable frame 42 includes a sleeve and a flexible part or an elastic part connected to the sleeve, the sleeve is configured to be sleeved over the endoscope, and the sliding contact part 53 is fixed on an inner side of the expandable frame, and is connected to the flexible part or elastic part; or the sliding contact part 53 may be fixed on an inner side of the sleeve. The flexible part or elastic part provides particular cushioning for the sliding contact part 53, so that the sliding contact part 53 is kept being electrically connected to the second electrically conductive part 52.

6. It may be selected as required that the electrical treatment part is the electric snare 221 or the electrocoagulation forceps 223 or the electric biopsy forceps 224 or a sphincterotome. The treatment apparatus for the endoscope of the present invention has a wide applicable range.

7. A layer of a conductive material is provided on an outer surface of the sheath 10, and the conductive material forms the second electrically conductive part 52. The type of the conductive material may be selected as required. The layer of the conductive material at least covers a peripheral surface of a part of the sheath 10. The layer of the conductive material may be made very thin to reduce an increase in an additional volume. Preferably, the layer of the conductive material is made smooth to facilitate the movement of the sheath 10 in the instrument passage of the endoscope.

8. The first cavity 11 and the second cavity 12 are provided on the sheath 10. The operating wire 20 is passed through the first cavity 11. The third electrically conductive part 54 is provided in the second cavity 12. The third electrically conductive part 54 is arranged in an axial direction along the sheath, and the third electrically conductive part 54 is electrically connected to the second electrically conductive part 52. The second cavity 12 is provided for special use by the third electrically conductive part 54, thereby ensuring that the third electrically conductive part 54 is electrically insulated from the second electrically conductive part 52 and the first electrode, thereby improving reliability.

9. The second cavity 12 has an annular shape surrounding the first cavity 11. The third conductive layer is distributed around the first cavity 11, so that an increase in the radius of the sheath 10 caused by the third electrically conductive part 54 may be restrained, so as to reduce the radius of the sheath 10.

10. The treatment apparatus for the endoscope further includes the feeding electrode 60. The feeding electrode 60 includes the active electrode 62 and the passive electrode 61. The electrical treatment part is electrically connected to the active electrode 62. The third electrically conductive part 54 is electrically connected to the passive electrode 61. The active electrode 62 supplies power to the electrical treatment part. The electrical treatment part performs an electrical operation on a human body. A current enters the human body from the electrical treatment part, is then guided out from the first electrically conductive part 51, and flows through the second electrically conductive part 52 to return to the passive electrode 61, so that the current flows by a minimum path in the human body.

11. The second electrically conductive part 52 surrounds the sheath 10 by one loop in a circumferential direction of the sheath 10, so that when the sheath 10 slides back and forth in the endoscope, desirable contact is kept between the second electrically conductive part 52 and the sliding contact part 53, and electrical contact is not affected even if the sheath 10 spins.

It should be noted that in this embodiment, the treatment apparatus for an endoscope may not include the second electrode. The second electrode may be externally connected to the treatment apparatus for an endoscope during use. In this case, the apparatus includes: a first electrode, including an electrical treatment part and an operating wire; and a sheath, provided on a surface thereof with a second electrically conductive part, where the second electrically conductive part is configured to be electrically connected to the first electrically conductive part on the endoscope. The arrangement of the remaining part of the sheath is the same as above. Details are not described herein again.

In this embodiment, the first electrically conductive part 51 is provided on the expandable frame 42 of the endoscope. An outer diameter of the expandable frame 42 is greater than an outer diameter of the endoscope body 401 of the endoscope, and the outer diameter of the endoscope body 401 of the endoscope is greater than an outer diameter of the sheath 10. Therefore, compared with the case in which the first electrically conductive part 51 is provided on the sheath 10, when the first electrically conductive part 51 is provided on the expandable frame 42, the first electrically conductive part 51 contacts a human body more easily to form an electrical loop, so as to ensure that "the electrical treatment part, the human body tissue, and the first electrically conductive part" form a stable current loop during surgery, thereby preventing the human body from burns.

Because the outer diameter of the expandable frame 42>the outer diameter of the endoscope body 401 of the endoscope>the outer diameter of the sheath 10, an area of contact between the first electrically conductive part 51 and the human body is large, a stronger surgical current may be used, and the surgery time is shortened. During surgery when a current is maintained within a safe current range, a length of safe contact of the first electrically conductive part 51 (the first electrically conductive part 51 provided inside the endoscope body 401) provided on the expandable frame 42 is far less than a length of the first electrically conductive part 41 provided on the sheath 10:

To facilitate description, for example, a diameter of a cutting head is 0.4 mm, an electrical cutting current is 680 mA, and an average surgery time is 2.1 s. According to the regulations in GB9706.4-2009 and IEC6060-2-2:2006, a safe threshold of a contact current for a human body is 1000 mA·s/cm².

To describe a relationship between an arrangement position of a contact electrode and a requirement of a safe contact length L, it is assumed that a common digestive endoscope with a relatively small size, that is, a duodenoscope, is chosen for measurement. An outer diameter of the duodenoscope is $d_1=1.25$ cm, and a maximum outer diameter of the treatment apparatus does not exceed an inner diameter of an endoscope channel $d_2=0.32$ cm.

(1) The first electrically conductive part 51 is provided on the sheath 10.

It is assumed that when the first electrically conductive part 51 is provided on the sheath 10 (that is, the first electrically conductive part 51 is provided on the peripheral surface of the sheath 10 and has an annular shape), an area of contact between the first electrically conductive part 51 and a human body is:

$$S_1 = \frac{90°}{360°} \cdot d_2 \cdot L \cdot \pi,$$

where $$\frac{90°}{360°}$$

means that assuming that the first electrically conductive part 51 has an annular shape surrounding the peripheral surface of the sheath 10 by one loop, a range of contact between the first electrically conductive part 51 and the human body tissue is ¼ of the arc surface (that is, only 90° of the circumferential 360° contacts human body tissue).

To satisfy the safe threshold of the contact current for the human body:

$$\frac{680 \text{ mA} \cdot 2.1 \text{ s}}{S_1} < 1000 \text{ mA} \cdot \text{s/cm}^2 = > \frac{1428 \text{ mA} \cdot \text{s}}{\frac{1}{4} \cdot 0.32 \text{ cm} \cdot \pi \cdot L_1} <$$

$$1000 \text{ mA} \cdot \text{s/cm}^2 = > L_1 \frac{1428 \text{ cm}}{80\pi} = 5.68 \text{ cm}.$$

Therefore, assuming that the first electrically conductive part 51 is provided on the sheath 10, to satisfy the safe threshold of the contact current for the human body, a length of the first electrically conductive body 51 in an axial direction of the sheath needs to be greater than 5.68 cm, or otherwise a deep burn may occur in the human body during normal surgery.

(2) The first electrically conductive part 51 is provided inside the endoscope body 401.

Assuming that the first electrically conductive part 51 is provided inside the endoscope body 401, a maximum area of contact with human body tissue is:

$$S_2 = \frac{90°}{360°} \cdot d_1 \cdot L \cdot \pi.$$

To satisfy the safe threshold of the contact current for the human body:

$$\frac{680 \text{ mA} \cdot 2.1 \text{ s}}{S_2} < 1000 \text{ mA} \cdot \text{s/cm}^2 => \frac{1428 \text{ mA} \cdot \text{s}}{\frac{1}{4} \cdot 1.25 \text{ cm} \cdot \pi \cdot L_1} <$$

$$1000 \text{ mA} \cdot \text{s/cm}^2 => L_2 \frac{1428 \text{ cm}}{312.5\pi} = 1.45 \text{ cm}.$$

As may be seen from above, the required length of the first electrically conductive part in the safe range is $L_1 \gg L_2$. When the first electrically conductive part is provided on the peripheral surface of the expandable frame, the safe contact length required to prevent a deep burn is shorter than the length of the first electrically conductive part provided on the peripheral surface of the sheath by approximately 75%, so that the safe contact length can be reached more easily for the contact electrode during surgery, and the surgery is safer and more effective.

Embodiment 2

Figure 6A:
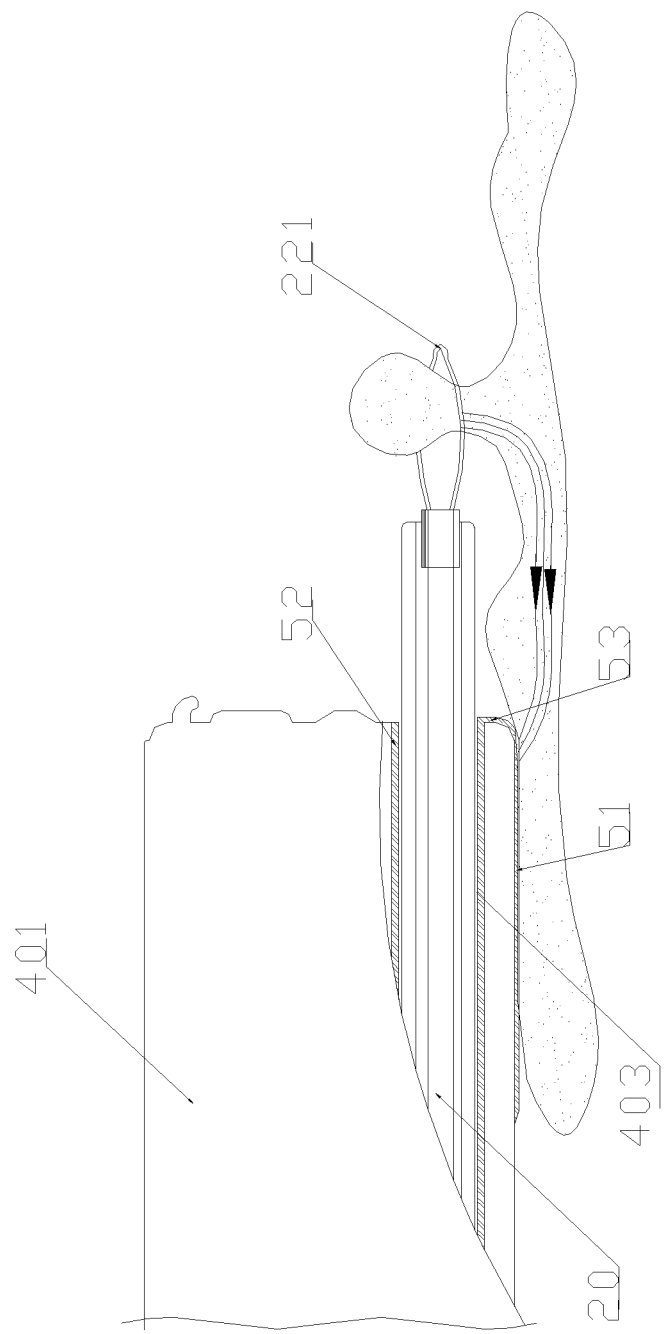
FIG. 6A to FIG. 6C are schematic diagrams of coordination between a treatment apparatus for an endoscope according to Embodiment 2 of the present invention and an endoscope.
Figure 6B:
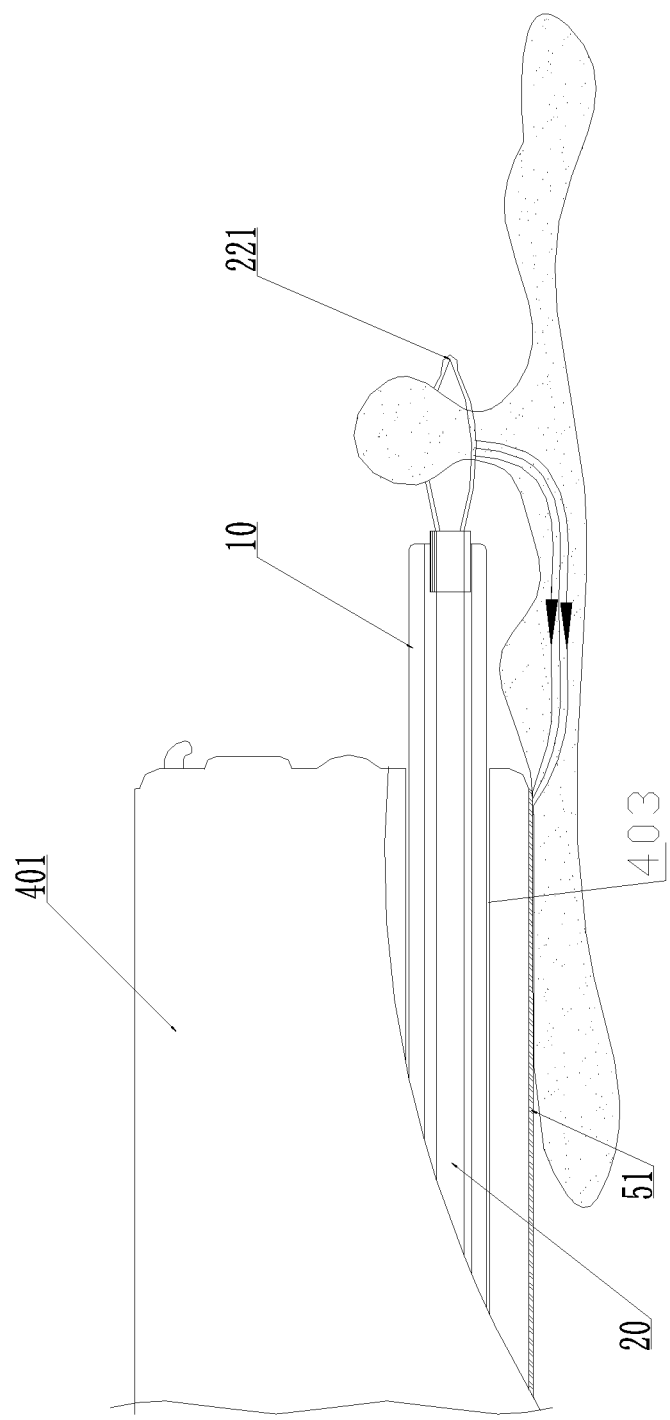
Figure 6C:
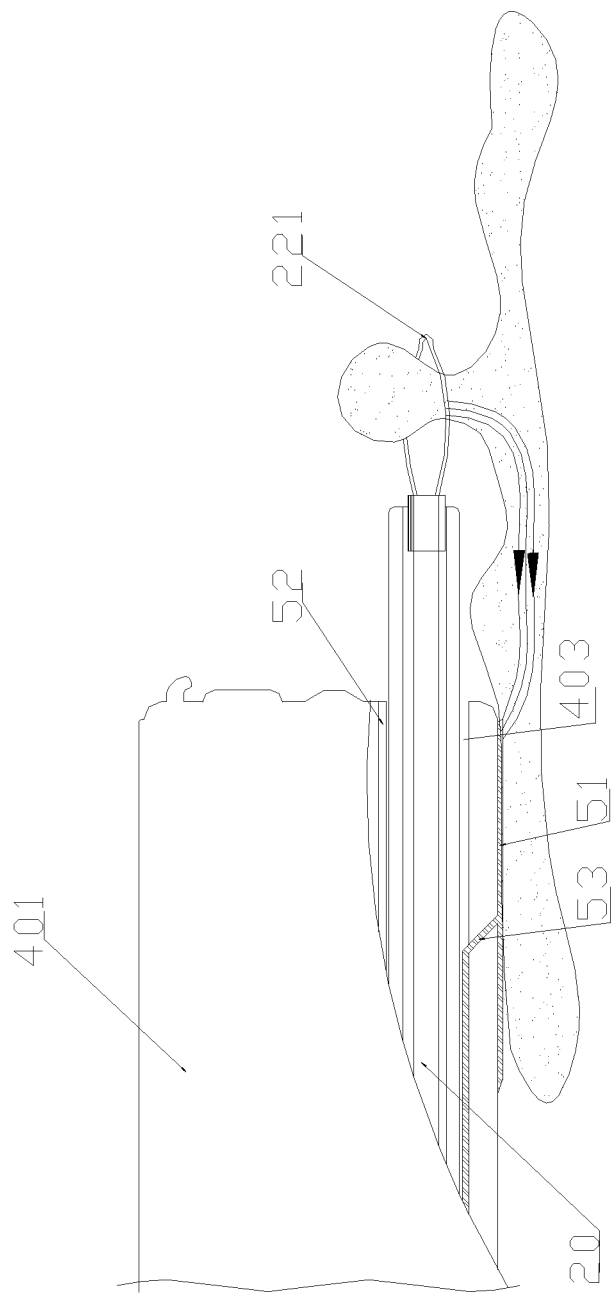

Embodiment 2 protects an endoscope. FIG. 6A, FIG. 6B, and FIG. 6C show three manners of guiding out a current via an endoscope. A fourth electrically conductive part 55 is provided inside the endoscope, and the fourth electrically conductive part 55 is electrically connected to the first electrically conductive part 51.

In a first implementation, the fourth electrically conductive part 55 is provided on an inner wall of the instrument passage 403 of the endoscope. The first electrically conductive part 51 is provided on a periphery of the camera 402 at the distal end of the endoscope body 401, and is electrically connected to the fourth electrically conductive part 55 in the instrument passage 403 directly or through the sliding contact part 53.

In a second implementation, the fourth electrically conductive part 55 is provided on an outer wall of the endoscope body 401 of the endoscope, and the fourth electrically conductive part 55 and the first electrically conductive part 51 are integrally provided on a periphery of the endoscope body 401 to form a whole.

In a third implementation, the fourth electrically conductive part 55 is provided on the inner wall of the instrument passage 403 of the endoscope. The first electrically conductive part 51 is provided on the periphery of the camera 402 at the distal end of the endoscope body 401, and the sliding contact part 53 passes through a side wall of the endoscope body 401 to electrically connect the first electrically conductive part 51 to the fourth electrically conductive part 55 in the instrument passage 403.

Preferred solutions and beneficial effects of this embodiment are as follows:

1. The endoscope includes the first electrically conductive part 51 provided on the outer surface of the endoscope. The first electrically conductive part 51 is configured to contact a human body. An instrument passage is provided in the endoscope. The instrument passage is configured to be passed through by a treatment apparatus for an endoscope. The fourth electrically conductive part 55 is provided inside the endoscope. The first electrically conductive part 51 is electrically connected to the fourth electrically conductive part 55. The first electrically conductive part 51 and the fourth electrically conductive part 55 provide the endoscope with an electrical path for guiding out a current in a human body. The current that enters the human body is guided out by the first electrically conductive part 51 and then guided out by the fourth electrically conductive part 55 in the endoscope.

Preferably, the second electrically conductive part 52 is configured to be electrically connected to the passive electrode 61 of the feeding electrode 60.

2. The first electrically conductive part 51 is directly provided inside the endoscope, the first electrically conductive part 51 may be embedded in an outer wall of the endoscope, or a layer of a conductive material may be provided on the peripheral surface of the endoscope, and the conductive material forms the fourth electrically conductive part 55.

3. A connecting through hole is formed in the endoscope. The peripheral surface of the endoscope and the instrument passage are communicated through the connecting through hole. The conductive material is provided in the connecting through hole to electrically connect to the first electrically conductive part 51 to the fourth electrically conductive part 55. After being guided out from the first electrically conductive part 51, the current that enters the human body sequentially passes through the conductive material in the connecting through hole and the fourth electrically conductive part 55 before being guided out.

4. The conductive material is provided on an end surface at the distal end of the endoscope to electrically connect the first electrically conductive part 51 to the fourth electrically conductive part 55. With such an arrangement, the end surface of the endoscope is also a position for contact with the human body. The end surface and the peripheral surface of the endoscope may both guide out a current from the human body when contacting the human body, so that an area of electrical contact with the human body may be enlarged.

Embodiment 3

Figure 22:
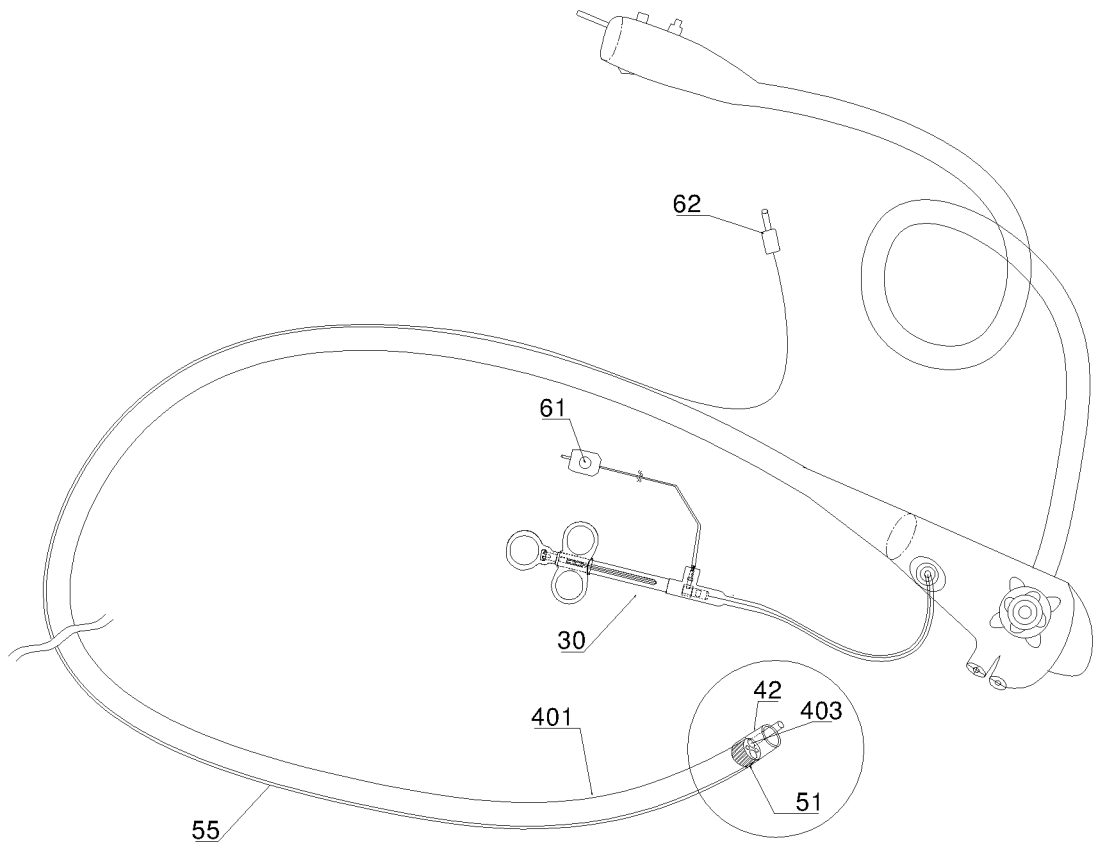
FIG. 22 is a schematic diagram according to Embodiment 3 of the present invention.
Figure 23:
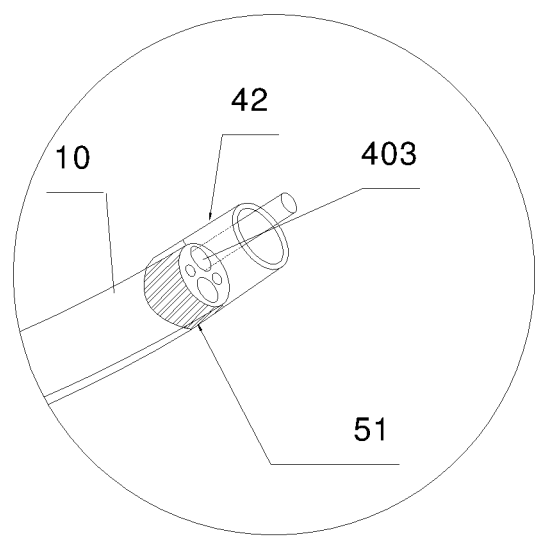
FIG. 23 is a partial enlarged view of FIG. 22.

Embodiment 3 protects an expandable frame for another endoscope. As shown in FIG. 22 and FIG. 23, a conductive material is provided on the peripheral surface of the expandable frame 42, and the conductive material forms the first electrically conductive part 51. A proximal end of the first electrically conductive part 51 is electrically connected to the fourth electrically conductive part 55. The fourth electrically conductive part 55 (which may be a conductor wire) is arranged along the endoscope body 401, is guided out from a proximal end of the endoscope body 401, and is electrically connected to the passive electrode 61. During working, the expandable frame 42 is installed on an ordinary endoscope, so that the expandable frame 42 is tightly attached to human body tissue. An existing monopolar instrument is inserted in the instrument passage 403 at the same time. A power supply is turned on after a focus is reached, and a working circuit is formed among an electrical treatment part of the monopolar instrument, tissue to be treated, and the first electrically conductive part 51, so as to complete surgical operations.

The differences between Embodiment 3 and Embodiment 1 lie in that the fourth conductive body instead of the sliding contact part is provided on the expandable frame, and the fourth conductive body is passed through the endoscope or provided outside the endoscope. Preferably, the fourth conductive body is a conductor wire, and the conductor wire is passed through the endoscope or provided outside the endoscope. The remaining shape of the expandable frame may be consistent with that in Embodiment 1. Such an expandable frame is conveniently used. The first electrically conductive part of the expandable frame is provided on a periphery of the expandable frame and contacts a human body and guides out a current in the human body. Next, the fourth electrically conductive part guides out the current in the human body, so as to provide a passage for guiding out the current from the human body. The fourth electrically conductive part may be easily installed inside the endoscope in a sleeving manner, it is not necessary to make additional changes to the endoscope, thereby achieving high compatibility and a wide use range.

Other Variants

The technical solutions in the foregoing embodiments may be implemented separately or implemented in combination, but is not limited to the foregoing embodiments. For example, the following variants may be used.

Figure 7B:
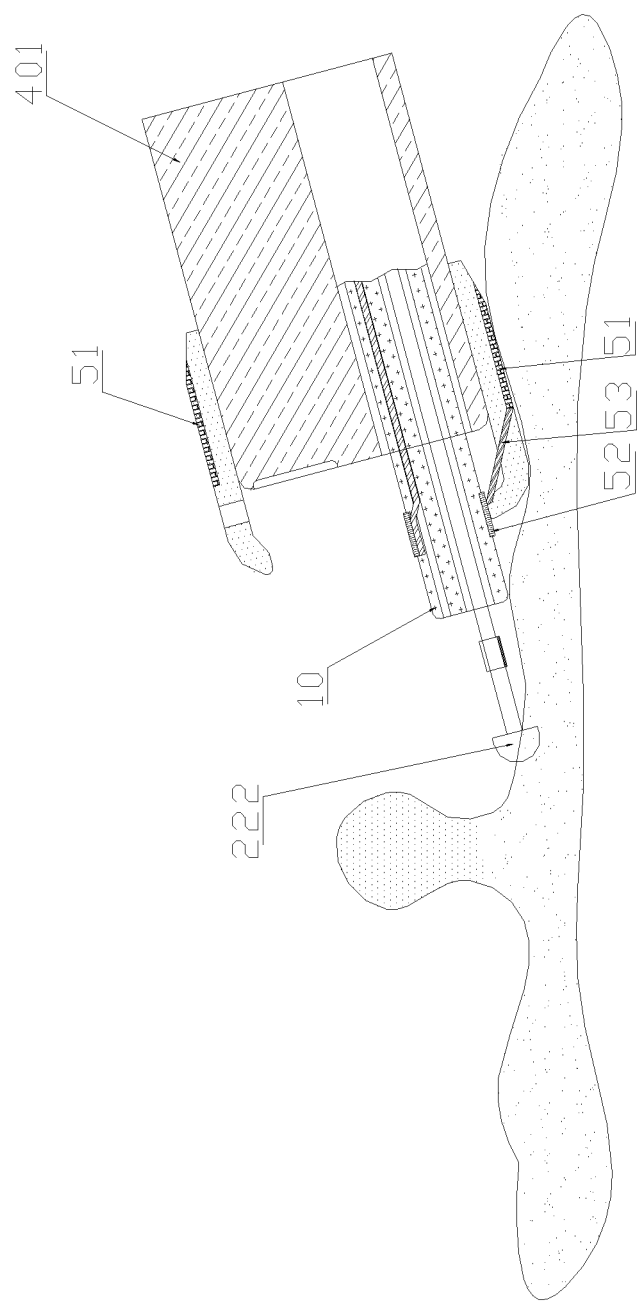
Figure 8A:
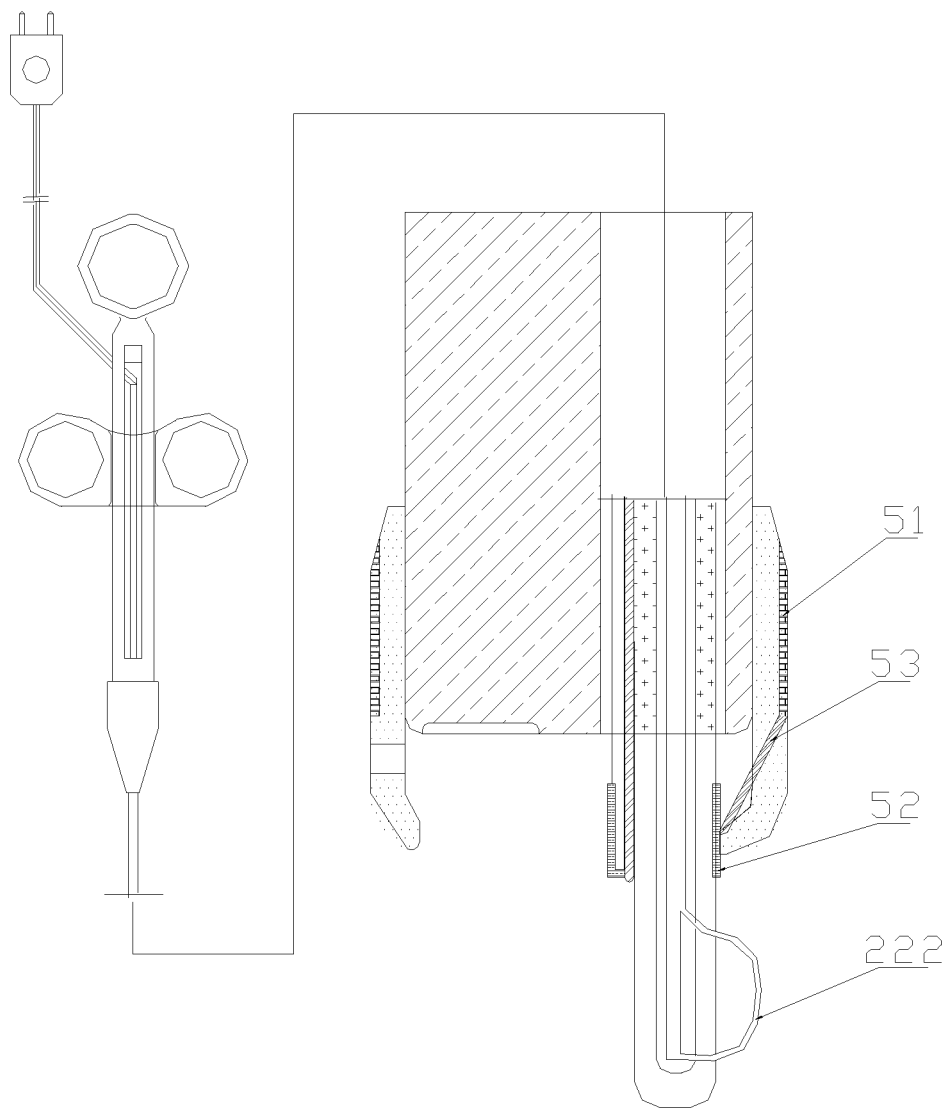
Figure 8B:
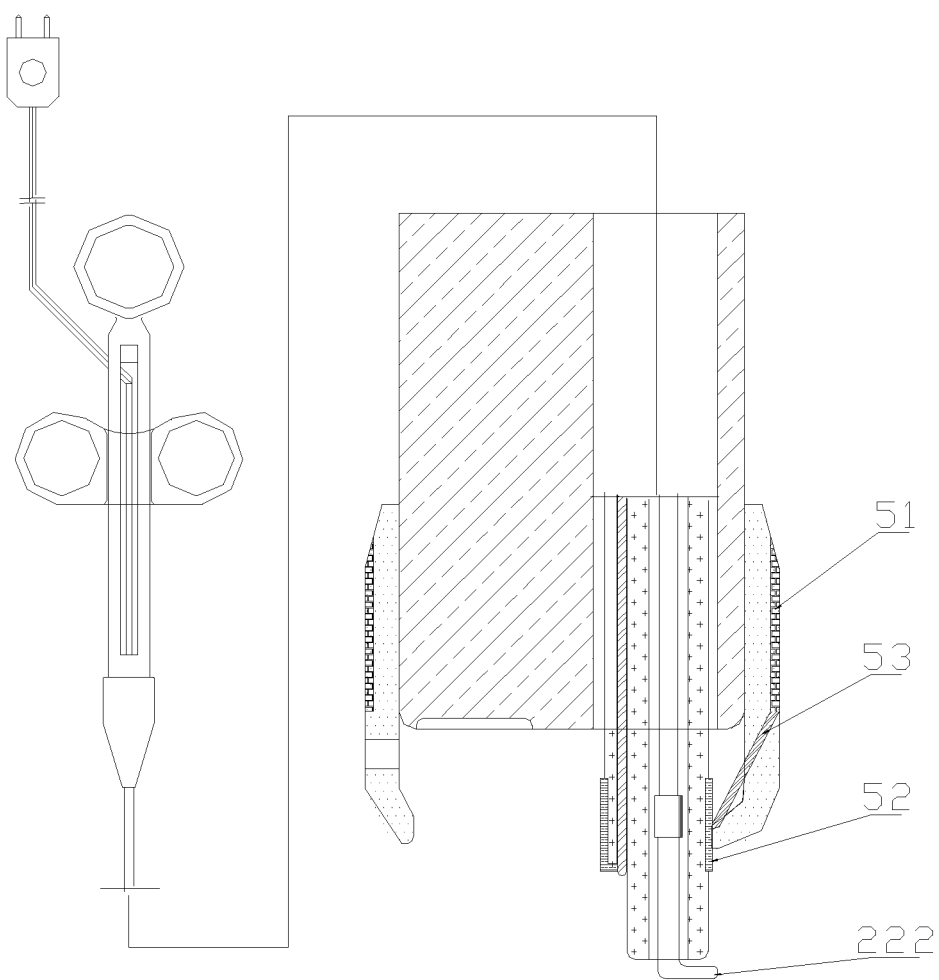
Figure 8C:
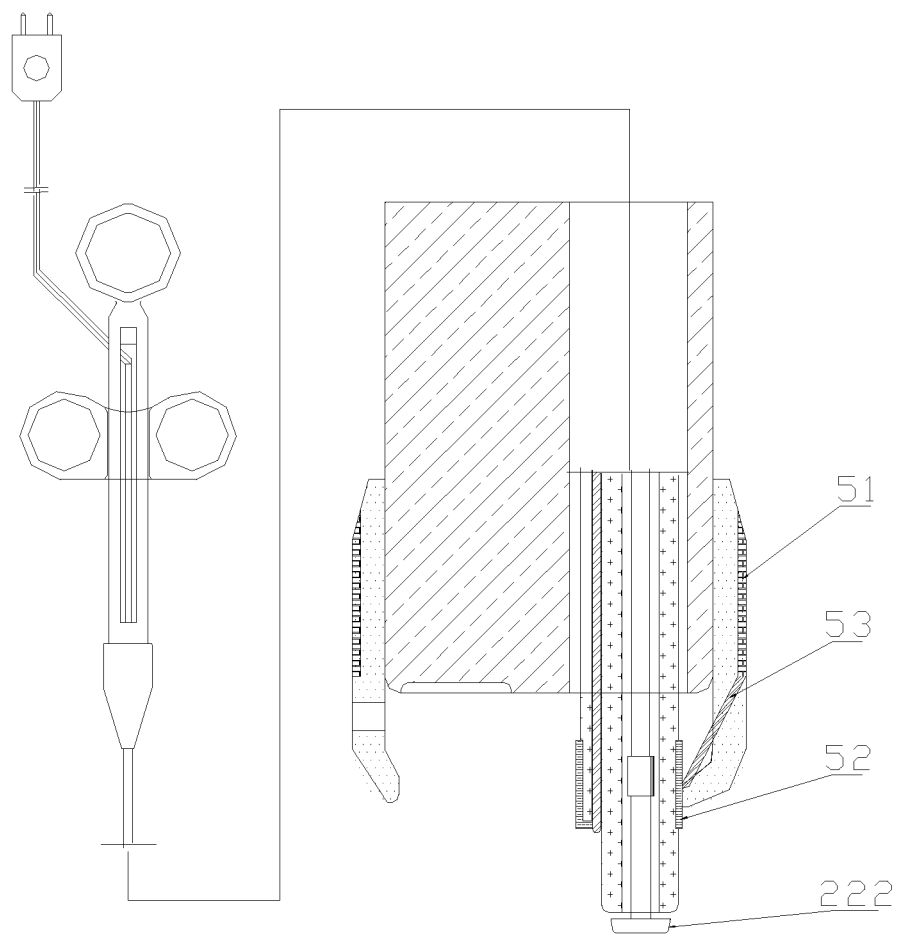
Figure 8D:
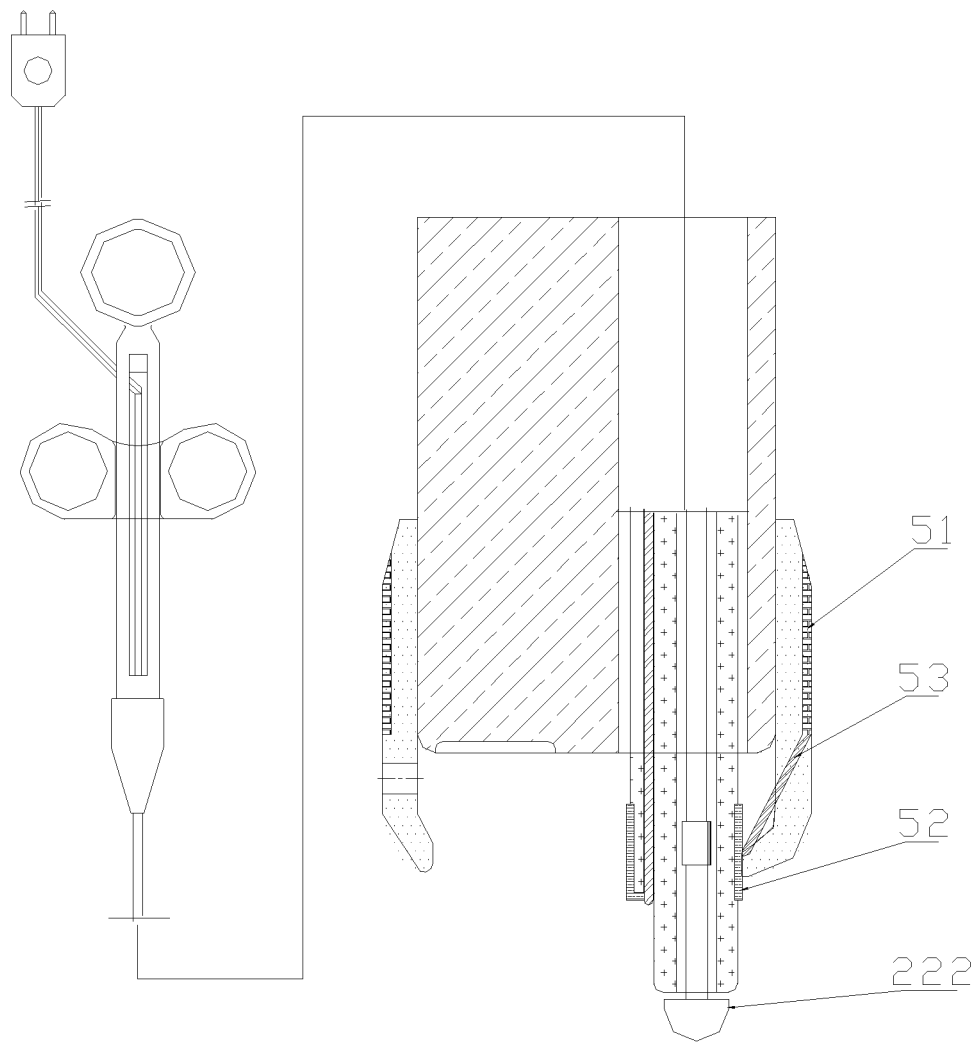
Figure 8E:
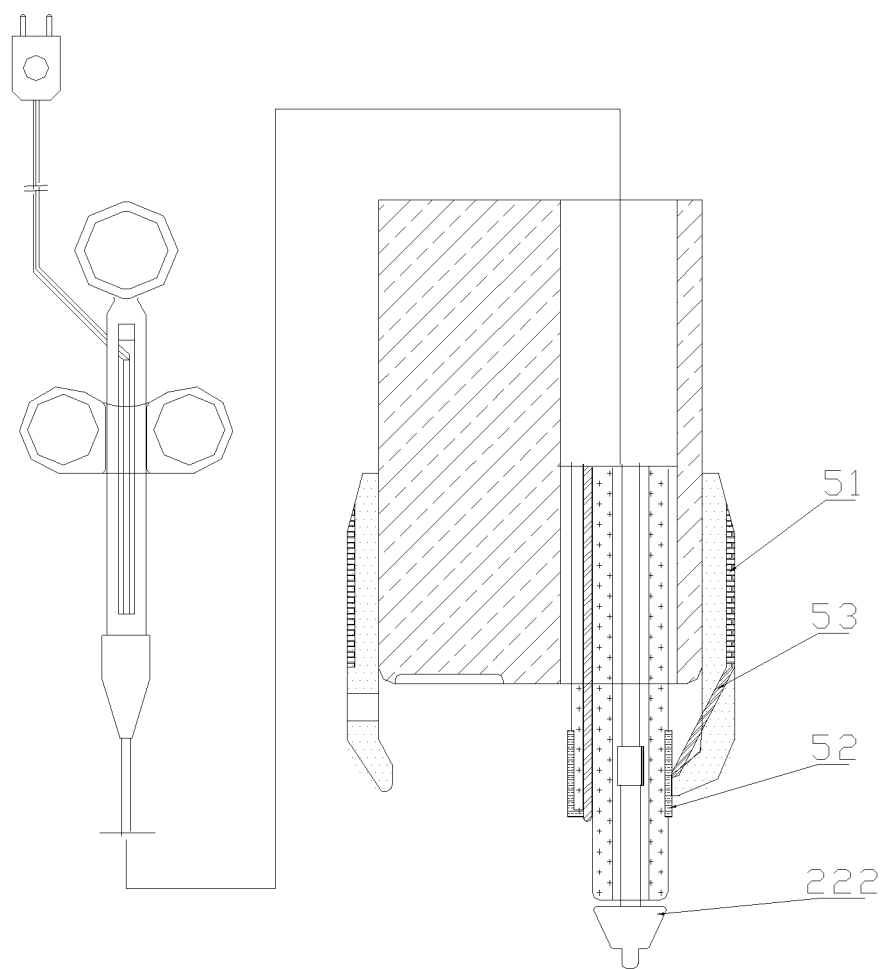
Figure 8F:
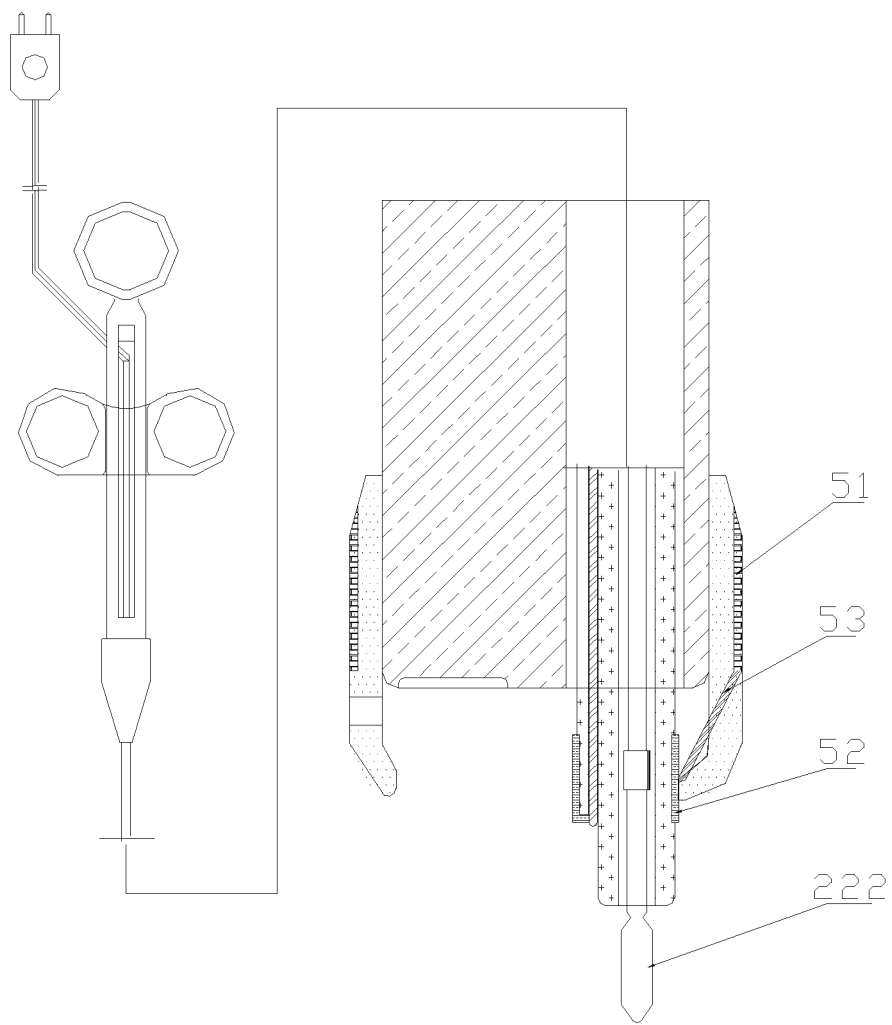

For example, to perform ESD surgery, as shown in FIG. 7A and FIG. 7B, the electric snare 221 is replaced with an ESD knife 222 having a head part extending in an axial direction of the operating wire. The head part 2221 may be a needle knife or may be a T-shaped knife, a star-shaped knife, provided that the head part is applicable to ESD surgery. FIG. 8A to FIG. 8F show several shapes of the electrical treatment part. The structural parts other than the ESD knife 222 are the same as those in the foregoing embodiments, and the details of these parts are omitted herein.

Figure 9:
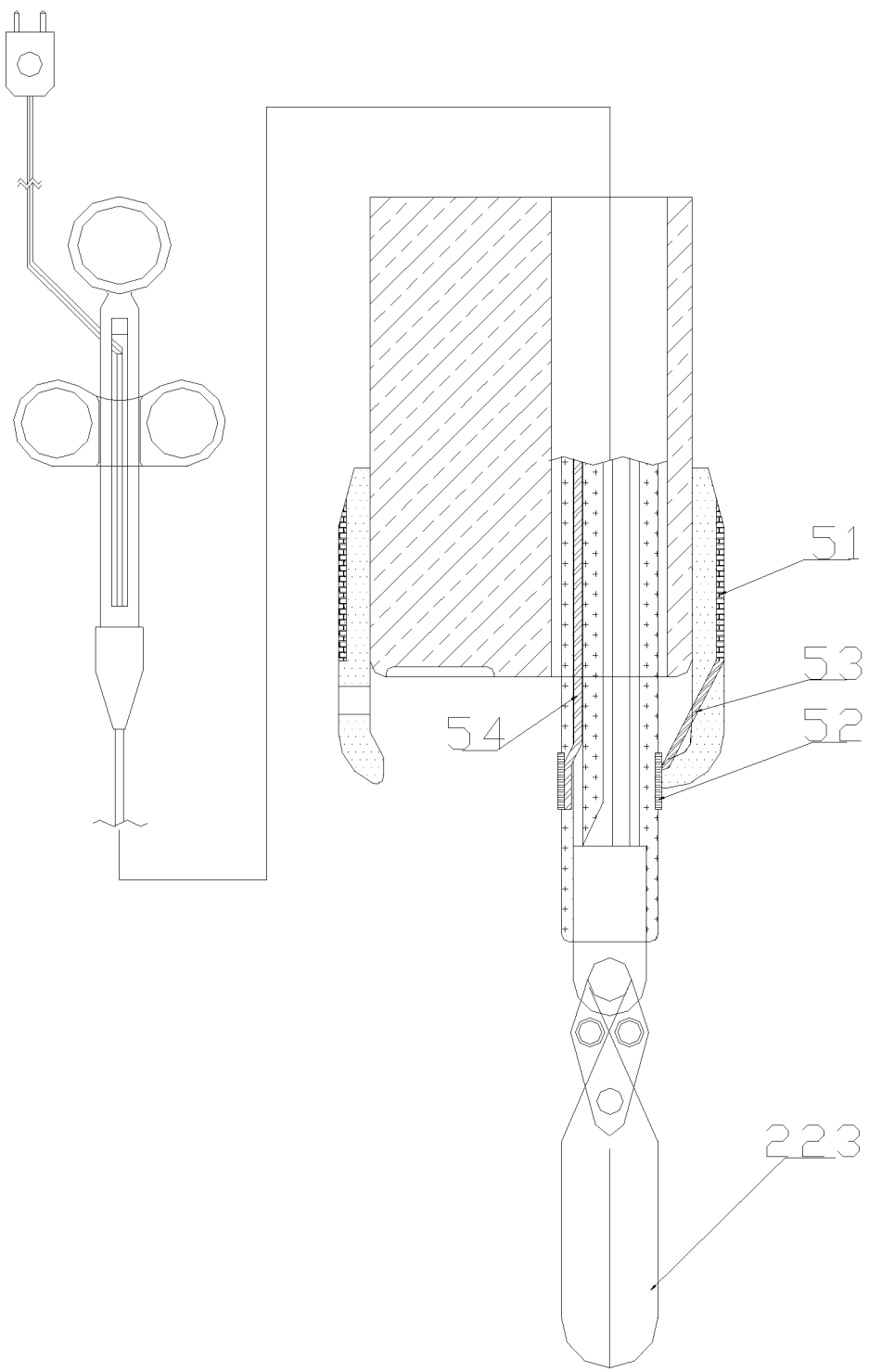
Figure 10:
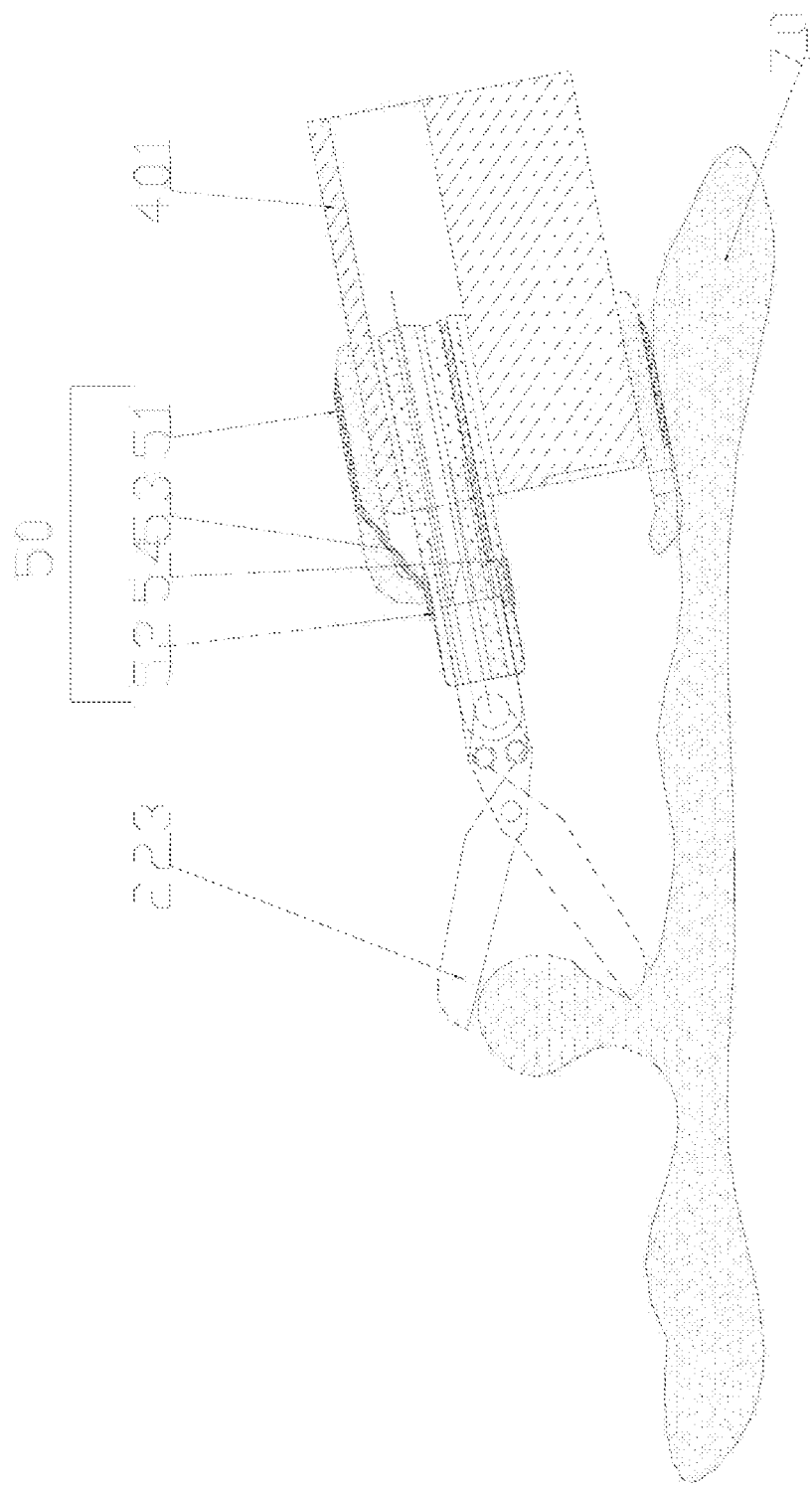

For another example, to perform hemostasis during surgery, as shown in FIG. 9 and FIG. 10, the electric snare 221 is replaced with the electrocoagulation forceps 223 having a pair of holding parts that can be opened or closed and can incise living tissue. The structural parts other than the electrocoagulation forceps 223 are the same as those in the foregoing embodiments, and the details of these parts are omitted herein.

Figure 11:
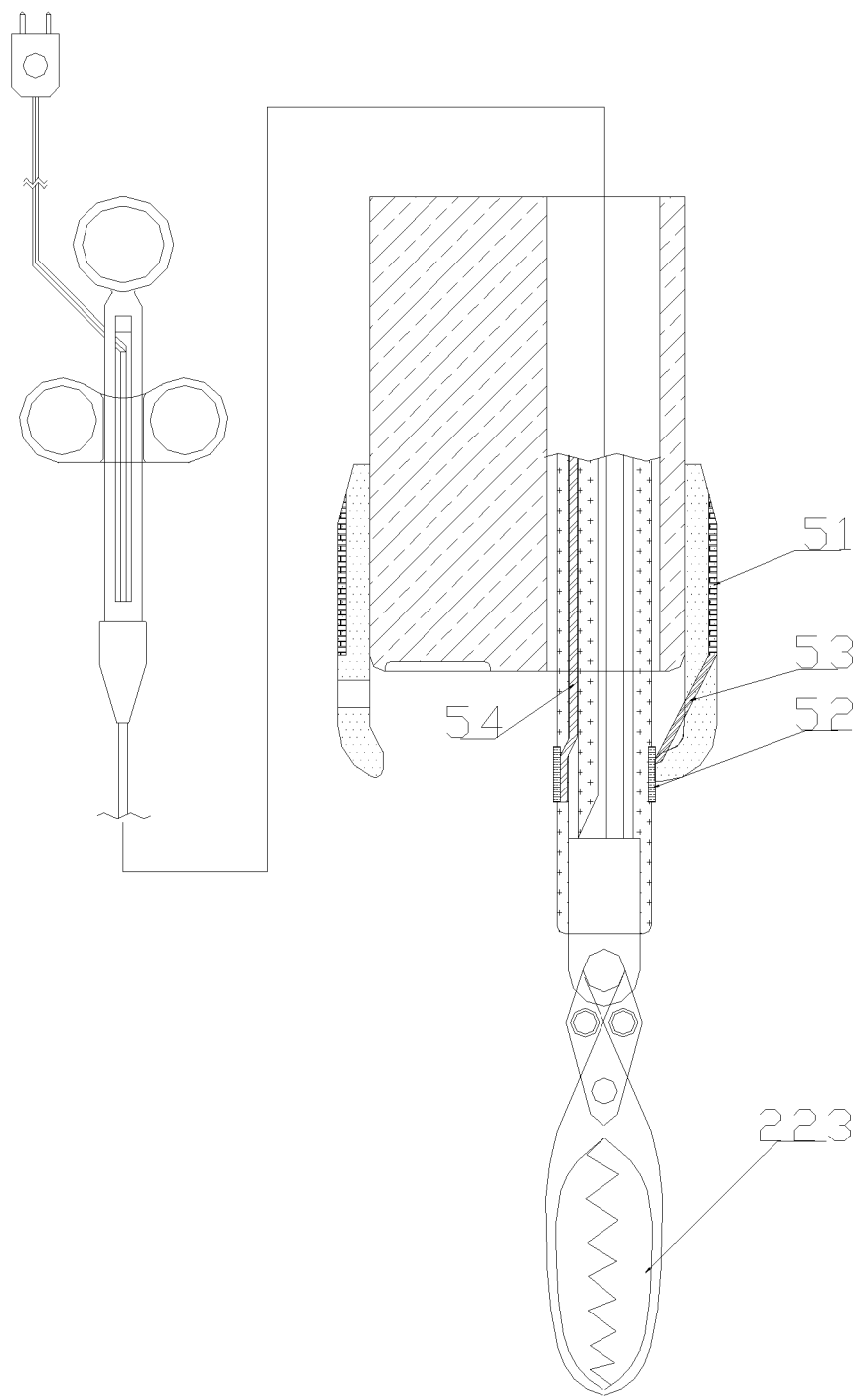

For still another example, to perform biopsy and hemostasis, as shown in FIG. 11 and FIG. 12, the electric snare 221 is replaced with the electric biopsy forceps 224. The structural parts other than the electric biopsy forceps 224 are the same as those in the foregoing embodiments, and the details of these parts are omitted herein.

Figure 13:
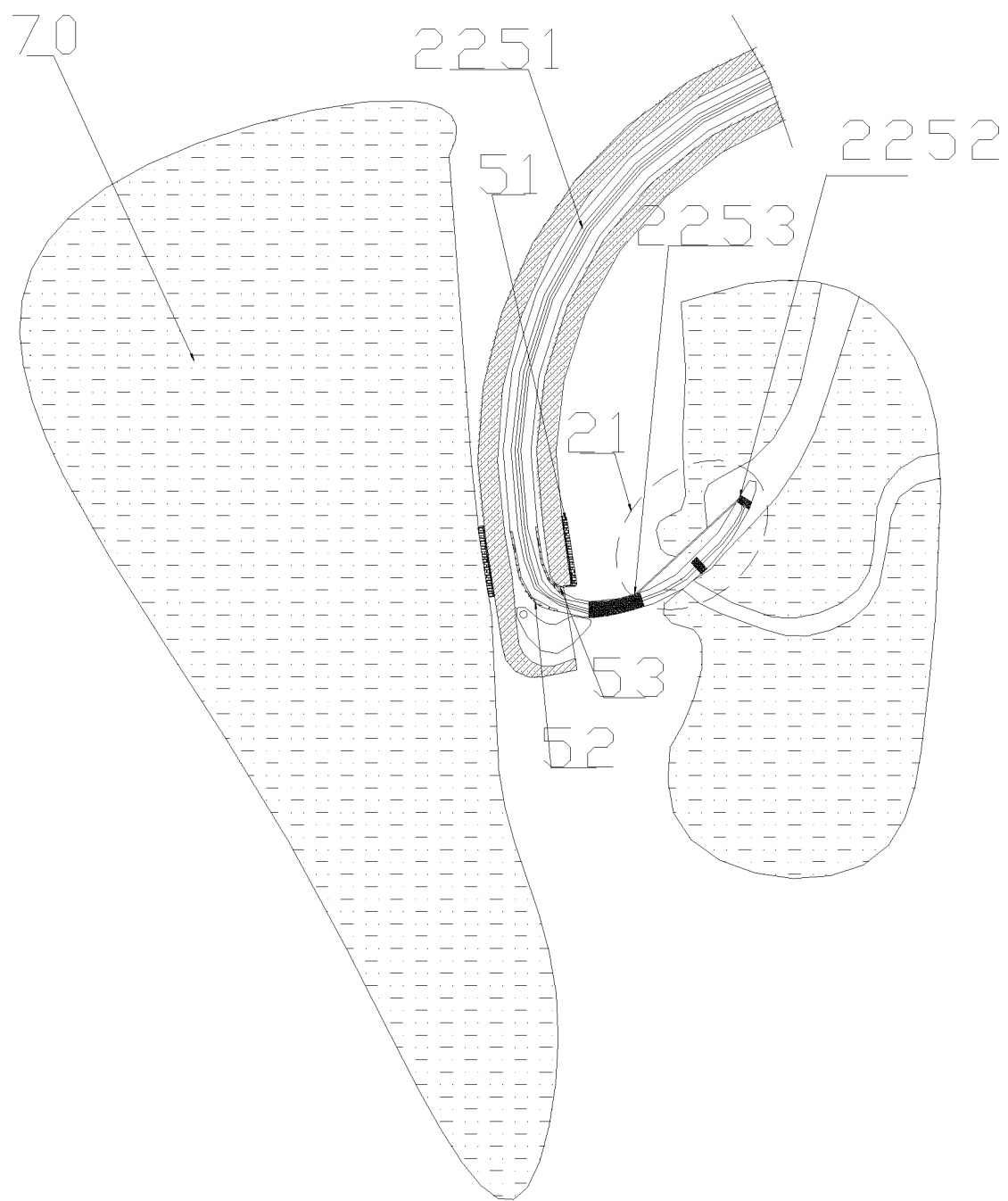

For yet another example, to perform endoscopic retrograde cholangiopancreatography (ERCP), as shown in FIG. 13, the electric snare 221 is replaced with a cutting wire 2252 having a papilla sphincterotome with a function of incising papillary sphincters. The papilla sphincterotome includes a conductor cavity 2251 extending longitudinally in the sheath 10 along the sheath 10. The conductor cavity 2251 is equivalent to the first cavity 11 in the embodiment of the electric snare 221. The cutting wire 2252 is accommodated in the conductor cavity. The cutting wire 2252 is passed through an anchor 2253 at a distance L from a distal end of the sheath and is joined to the distal end of the sheath, so that the cutting wire 2252 and the distal end form a bow-shaped cutting part 21. The cutting wire 2252 is securely joined to the sheath 10 at the anchor. A proximal end of the cutting wire 2252 is electrically connected to the operating wire 20 having conductive performance. The remaining structural parts in this embodiment are the same as those in the foregoing embodiments, and the details of these parts are omitted herein.

Figure 24:
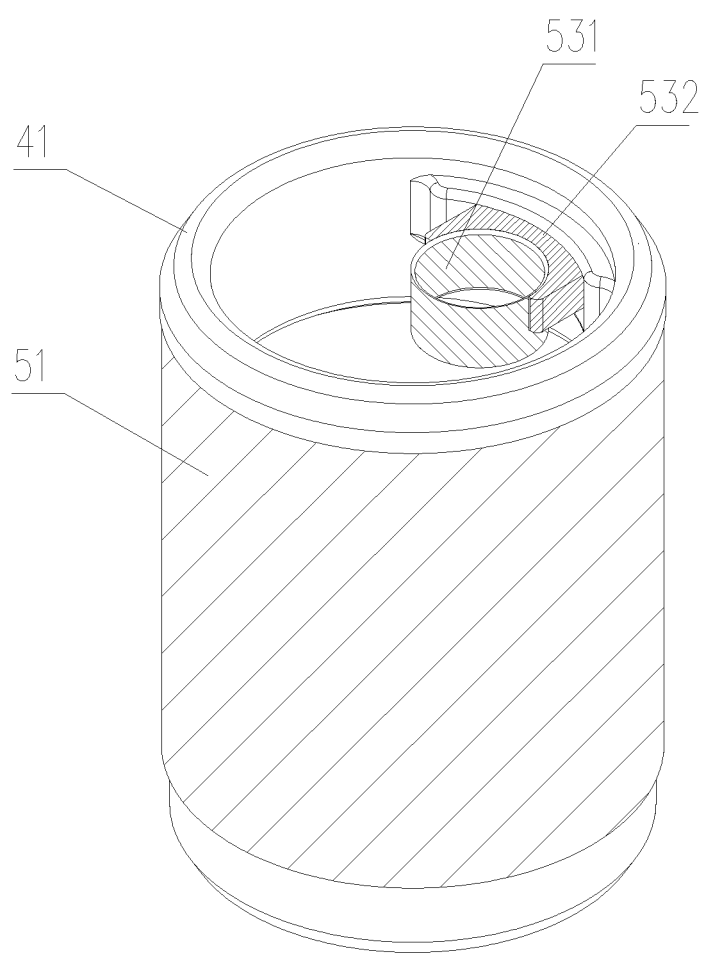
FIG. 24 is a schematic diagram according to another implementation of the present invention.
Figure 25:
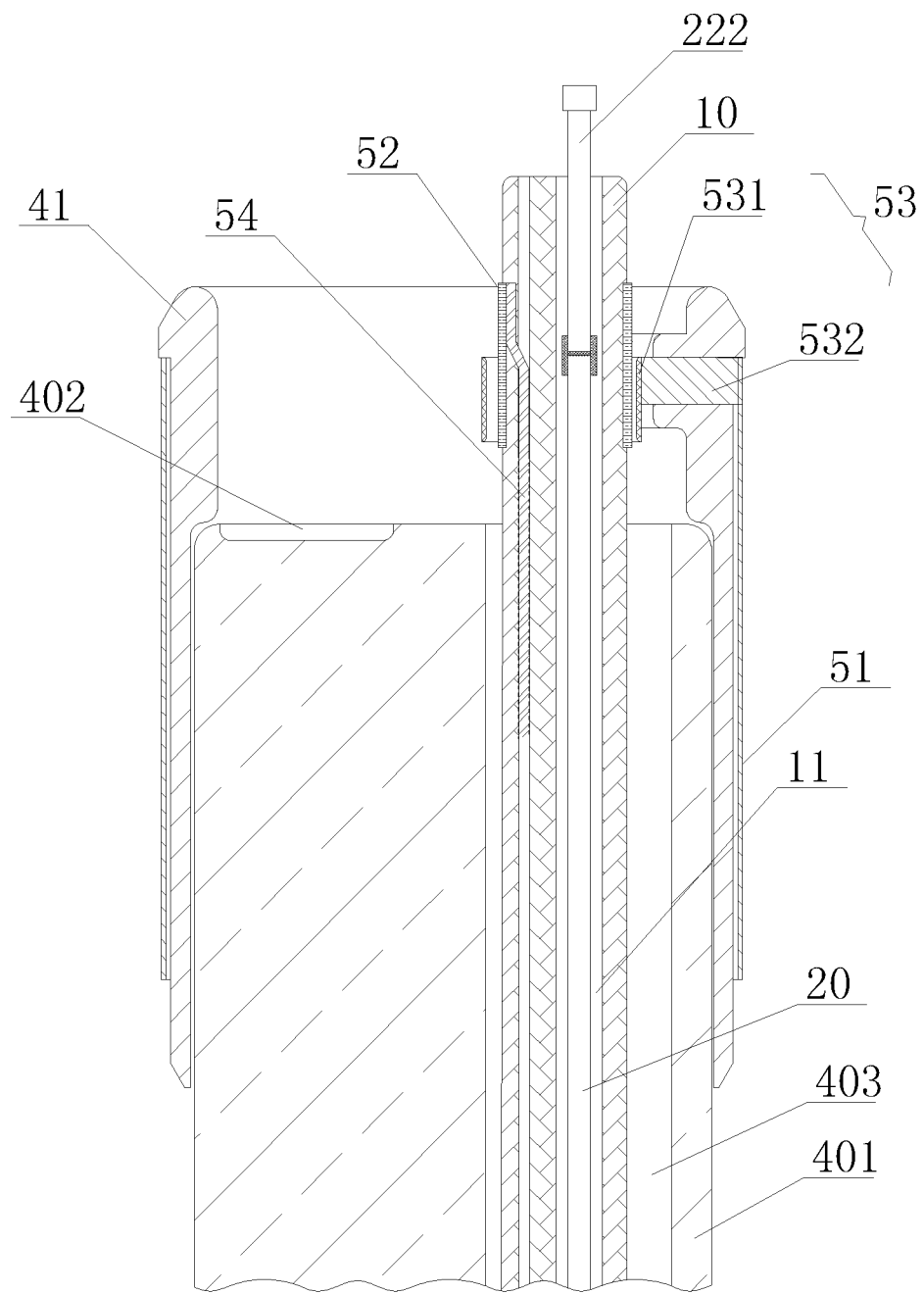
FIG. 25 is a partial sectional view of FIG. 24.
Figure 26:
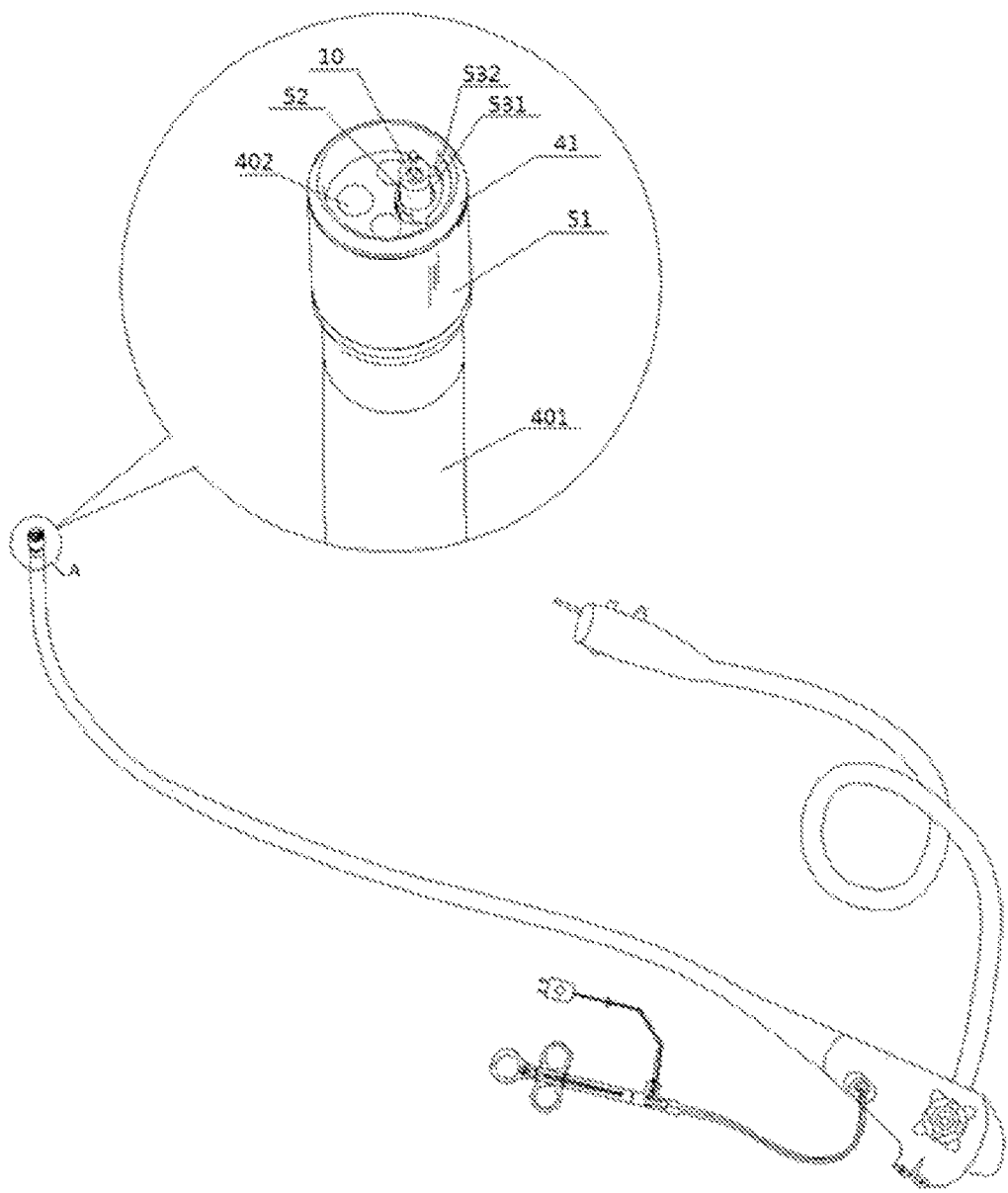
FIG. 26 is a schematic diagram of an overall structure of the implementation in FIG. 24.

In addition, preferably, as shown in FIG. 24 to FIG. 26, the sliding contact part 53 may further include a fifth electrically conductive part 531 and a sixth electrically conductive part 532. The fifth electrically conductive part 531 may ensure a stable connection between the sliding contact part and the second electrode. The sixth electrically conductive part 532 is configured to be electrically connected to the first electrically conductive part 51. In FIG. 24 to FIG. 26, the fifth electrically conductive part is a steel spring ball. A highest point of the steel spring ball protrudes from an extension line of the instrument passage of the endoscope, and a tail of the steel spring ball is inserted in the expandable frame. The fifth electrically conductive part is electrically connected to the first electrically conductive part 51 through the sixth electrically conductive part. In addition, there may be another implementation of the fifth electrically conductive part 531. For example, the fifth electrically conductive part 531 may be provided as an electrically conductive ring. A central line of the electrically conductive ring is consistent with a central axis of the instrument passage of the endoscope, and an inner diameter of the electrically conductive ring is consistent with an inner diameter of the instrument passage. In this case, the sixth electrically conductive part 532 is electrically connected to the first electrically conductive part 51 and the electrically conductive ring. The electrically conductive ring is used to keep stable contact of the electrically conductive parts in all directions and further reduce manufacturing costs. The fifth electrically conductive part may also be an electrically conductive prism. A central line of the electrically conductive prism is consistent with a longitudinal axis of the endoscope, and the electrically conductive prism protrudes from an axial extension line of a wall of the instrument passage of the endoscope. Alternatively, the fifth electrically conductive part may be an insertion tube inserted at a distal end of the instrument passage, and may ensure stable matching between the sliding contact part and the instrument passage.

In addition, the first electrically conductive part 51 may also be arranged in another manner.

Figure 14:
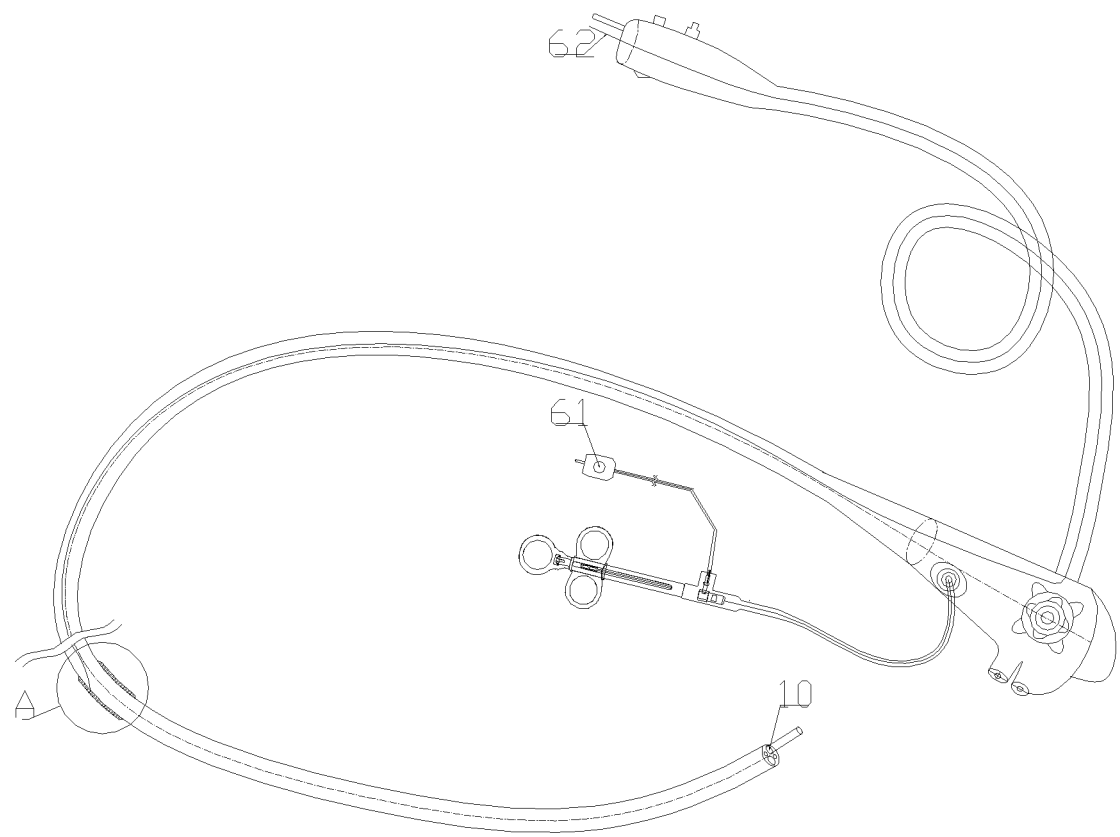
FIG. 14 is a schematic diagram according to another implementation of the present invention.
Figure 15:
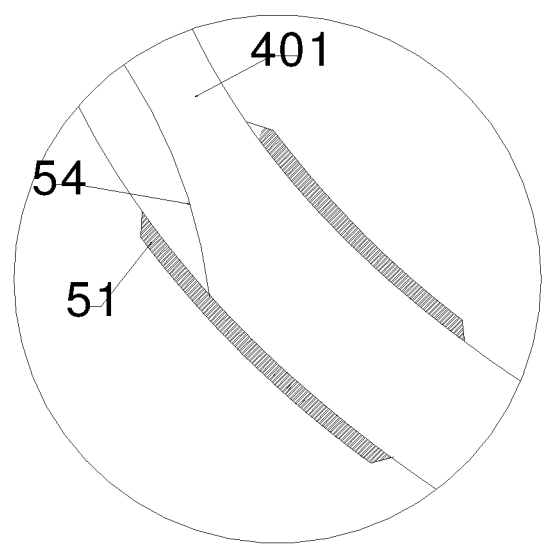
FIG. 15 is an enlarged view of A in FIG. 14.

In a variant, as shown in FIG. 14 and FIG. 15, the first electrically conductive part 51 is provided in the middle of the endoscope body 401 of the endoscope. The return conductor 54 is provided longitudinally along the endoscope body 401, and is electrically connected to the first electrically conductive part 51. The feeding power supply 60 includes the passive electrode 61 and the active electrode 62. The passive electrode 61 is electrically connected to the third electrically conductive part 54 (or the fourth electrically conductive part 55), and is guided out at the proximal end of the endoscope body 401. In addition, the active electrode 62 is electrically connected to a high-frequency treatment part, and is guided out from the drive part 30. Although the third electrically conductive part 54 (or the fourth electrically conductive part 55) is provided inside the endoscope body 401 in this embodiment, a specific position of arranging the third electrically conductive part 54 is not limited, provided that the third electrically conductive part 54 (or the fourth electrically conductive part 55) can be electrically connected to the first electrically conductive part. The third electrically conductive part 54 (or the fourth electrically conductive part 55) may be arranged on the sheath 10, and is electrically connected to the first electrically conductive part 51 through a conduction mechanism provided on an inner side of the first electrically conductive part 51. In this case, the passive electrode 61 and the active electrode 62 are both guided out from the drive part 30.

Figure 16:
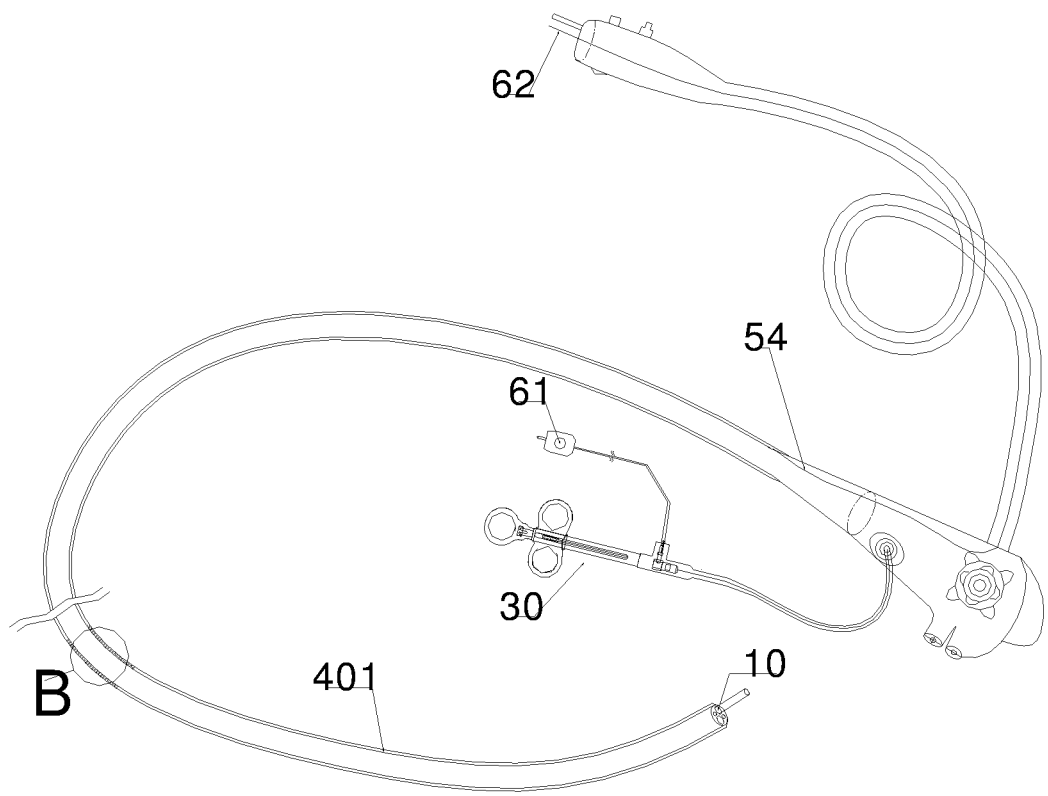
FIG. 16 is a schematic diagram according to another implementation of the present invention.
Figure 17:
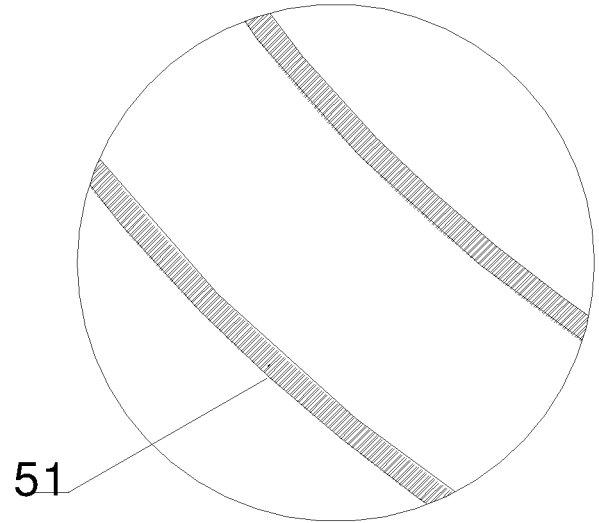
FIG. 17 is an enlarged view of B in FIG. 16.

In another variant example, FIG. 16, FIG. 17, and FIG. 6B show an endoscope. A first electrically conductive part 51 of the endoscope covers an outer surface of the endoscope body 401. The return conductor 54 is electrically connected to the proximal end of the first electrically conductive part 51, and is guided out from the proximal end of the endoscope body 401 to the passive electrode 62. The active electrode 61 is electrically connected to the high-frequency treatment part, and is guided out from the drive part 30.

Figure 18:
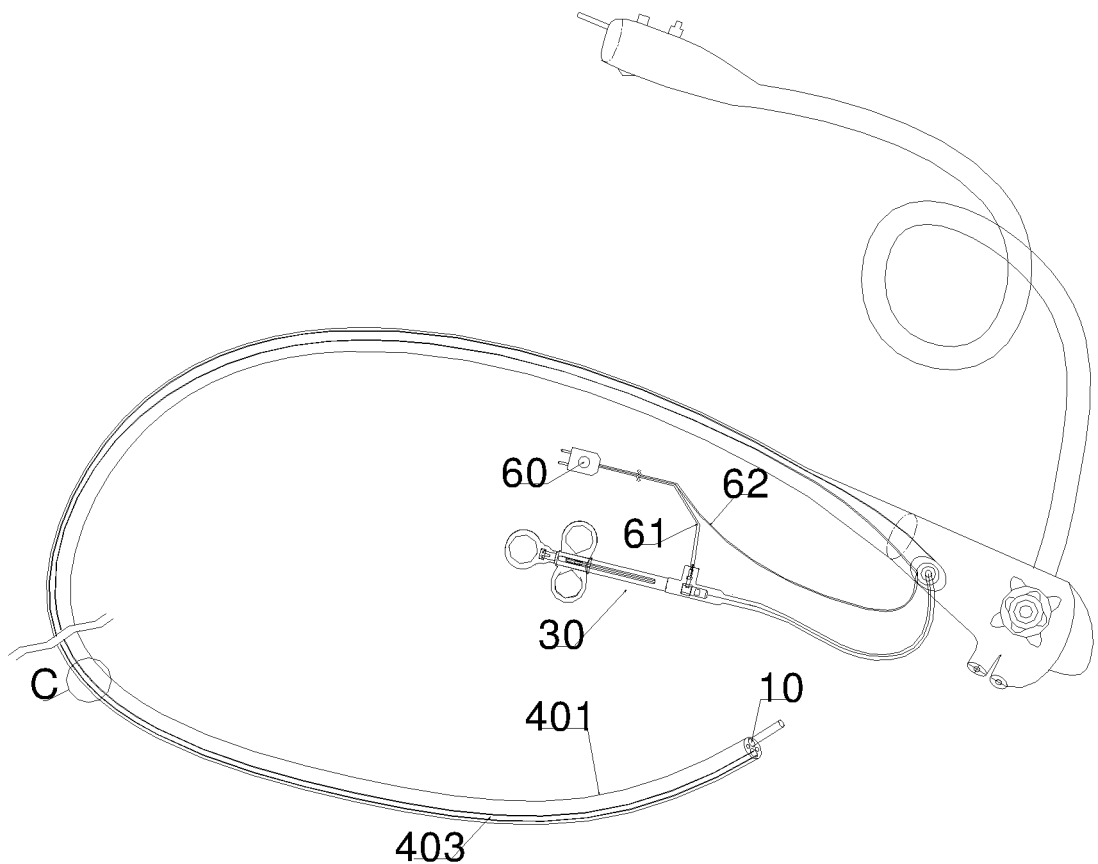
FIG. 18 is a schematic diagram according to another implementation of the present invention.
Figure 19:
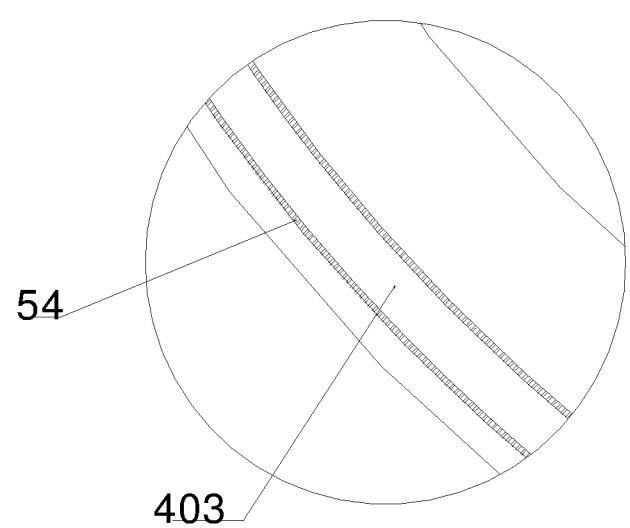
FIG. 19 is an enlarged view of C in FIG. 18.

In another variant example, FIG. 18, FIG. 19, and FIG. 6A show another endoscope. The first electrically conductive part 51 of endoscope covers a peripheral surface at the distal end of the camera 401. The return conductor 54 is arranged on an inner wall of the instrument passage 403 and is electrically connected to the passive electrode 61, and the return conductor 54 and the active electrode 62 are then guided out together from the drive part 30.

Figure 20:
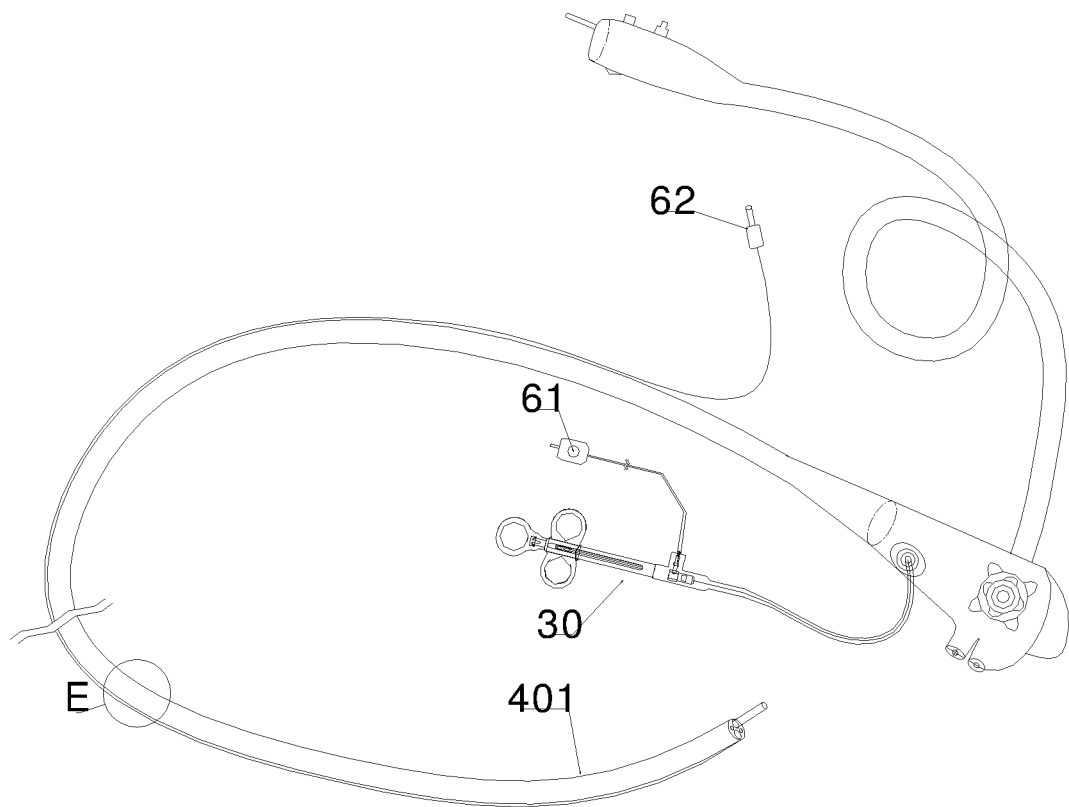
FIG. 20 is a schematic diagram according to another implementation of the present invention.
Figure 21:
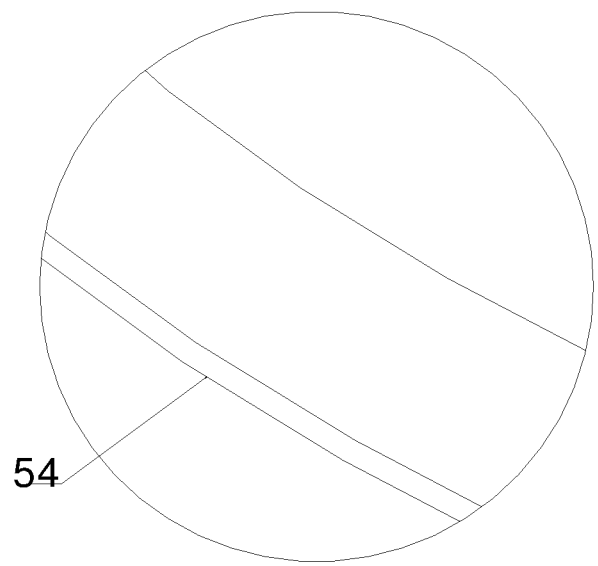
FIG. 21 is an enlarged view of E in FIG. 20.

In another variant example, FIG. 20 and FIG. 21 show another endoscope. The return conductor 54 of the endoscope is a conductor wire arranged on an outer side of the endoscope body 401, and during use, the return conductor 54 coordinate with a high-frequency treatment apparatus having the first electrically conductive part 51. The conductor wire is electrically connected to the first electrically conductive part 51.

Embodiment 4

Differences between Embodiment 4 and Embodiment 1 are as follows:

As shown in FIG. 27 to FIG. 30, the application structure for an endoscope further includes a tissue operation mechanism 70. The tissue operation mechanism 70 is installed on the expandable frame 42. The expandable frame 42 is sleeved over the endoscope body 401 of the endoscope 40. A mechanism installing hole 411 is further formed in the expandable frame. The tissue operation mechanism 70 is passed through the mechanism installing hole 411. There are two first electrically conductive parts 51. One first electrically conductive part 51 is provided on the tissue operation mechanism, and the other first electrically conductive part 51 is provided on the peripheral surface of the expandable frame. The first electrically conductive part 51 of the tissue operation mechanism 70 is electrically connected to the first electrically conductive part 51 of the expandable frame 42. The first electrically conductive part 51 provided on the tissue operation mechanism 70 may be directly provided on an outer surface of the tissue operation mechanism 70, or an independent mechanism may be provided as the first electrically conductive part 51 on the tissue operation mechanism 70, provided that the first electrically conductive part 51 can be electrically connected to human body tissue. Specific forms are not limited.

The fourth electrically conductive part 55 is further provided on the tissue operation mechanism 70. The first electrically conductive part 51 and the fourth electrically conductive part 55 that are provided on the tissue operation mechanism 70 are electrically connected.

The first electrically conductive part 51 is configured to contact a human body to form an electrical loop. One or both of the first electrically conductive part 51 on the expandable frame 42 and the first electrically conductive part 51 of the tissue operation mechanism 70 electrically contacts human body tissue, so as to guide out a current from the human body to form the loop. Two first electrically conductive parts 51 are provided to make it easier to electrically contact human body tissue, thereby ensuring the security of surgery and avoiding burning of human body tissue.

Figure 27:
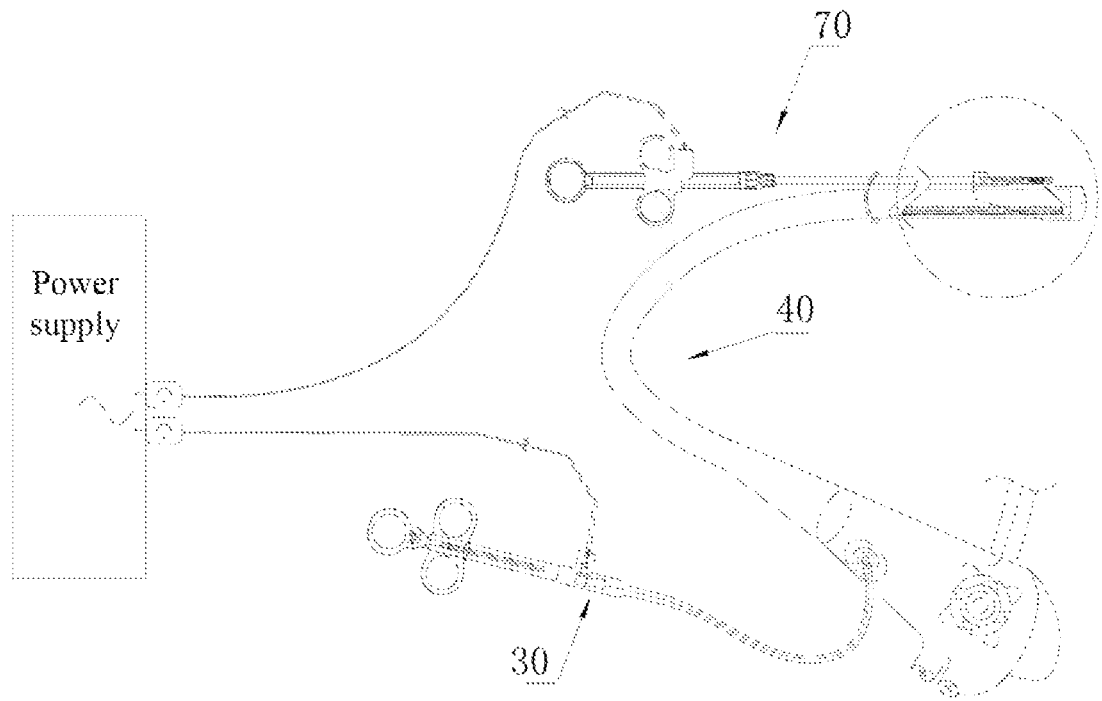
FIG. 27 is a structural diagram 1 according to Embodiment 4 of the present invention.

As shown in FIG. 27, the tissue operation mechanism 70 is installed outside the endoscope, and the tissue operation mechanism 70 and the electrical treatment part (the electrocoagulation forceps 223) are connected to the same high-frequency power supply.

The tissue operation mechanism 70 is an apparatus from performing operations on human body tissue. Any type of tissue operation mechanism 70 may be selected according to operations required in surgery, and the operations include, but are not limited to, holding tissue, snaring tissue, pushing tissue to create a space, pulling tissue, and fixing the position of tissue. Because a surgical procedure usually includes several operations, and an apparatus that can complete an operation other than the function of the treatment apparatus for an endoscope in the present invention may be regarded as a tissue operation apparatus in the present invention.

Figure 28:
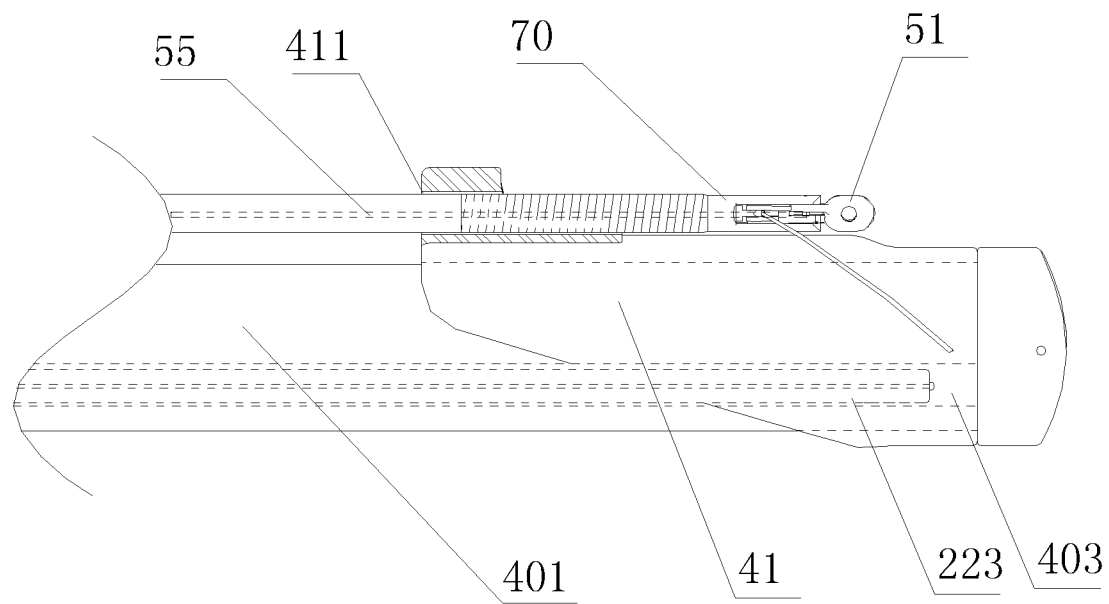
FIG. 28 is a partial enlarged view of a circle in FIG. 24.

A method of using the treatment apparatus for an endoscope is as follows:

(1). FIG. 27 and FIG. 28 show a state before the treatment apparatus enters a human body cavity. The treatment apparatus for an endoscope is accommodated in the instrument passage 403 of the endoscope body 401. The tissue operation mechanism 70 does not extend beyond a front end of the endoscope body 401. A holding mechanism is provided at a front end of the tissue operation mechanism 70. The holding mechanism is conductive. The holding mechanism at the front end of the tissue operation mechanism 70 forms the first conductor part 51. A conductive wire is provided in the tissue operation mechanism 70 or the tissue operation mechanism 70 is conductive. The conductive wire or the tissue operation mechanism 70 forms the fourth conductor part 55 (FIG. 28 shows a case in which the conductive wire is provided in the tissue operation mechanism 70).

Figure 29:
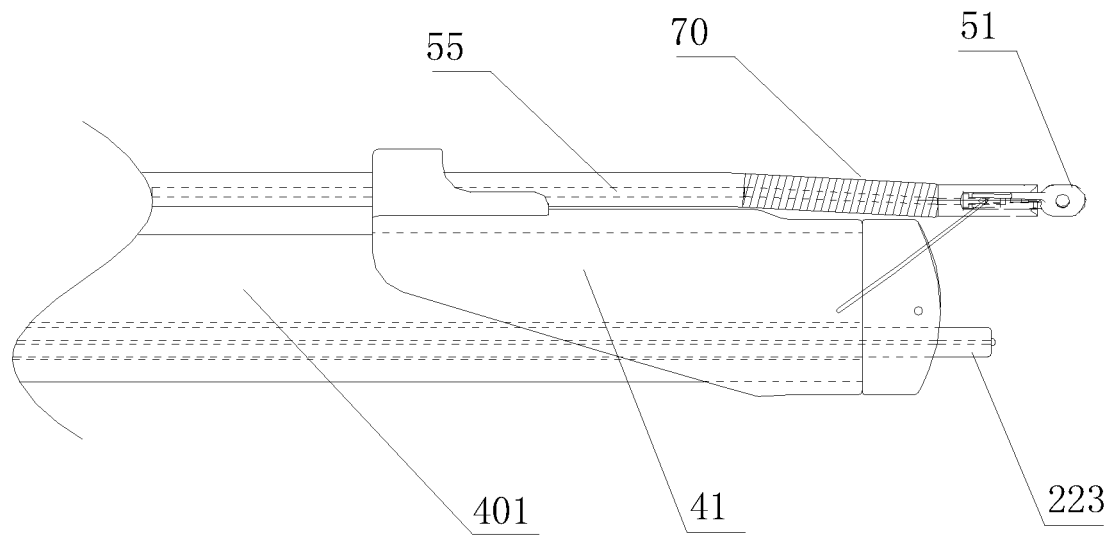
FIG. 29 is a structural diagram 2 according to Embodiment 4 of the present invention.
Figure 30:
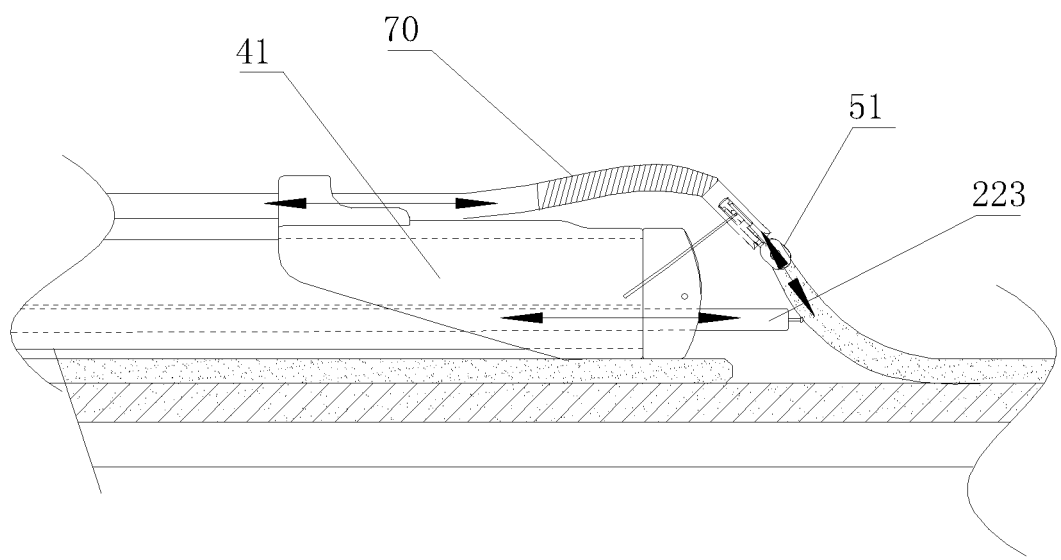
FIG. 30 is a structural diagram 3 according to Embodiment 4 of the present invention.

(2). The position of a focus is reached. The electrocoagulation forceps 223 and the tissue operation mechanism 70 of the treatment apparatus for an endoscope are deployed. As shown in FIG. 29, the first electrically conductive part 51 first electrically contacts a human body, and the electrocoagulation forceps 223 then contacts the human body. When the electrocoagulation forceps 223 is used to operate on the human body, there is usually hindrance or blockage of human body tissue or human body tissue beats with breathing pulses. Therefore, the tissue operation mechanism 70 is first used to operate on the human body tissue (push the tissue to create a space, fix the tissue or the like). FIG. 30 shows that the tissue operation mechanism 70 pushes tissue to create a space. While the tissue operation mechanism 70 is used to operate on the human body tissue, the first electrically conductive part 51 naturally contacts the human body. That is, the first electrically conductive part 51 electrically contacts the human body. The electrocoagulation forceps 223 is then operated to operate on the human body. At this time, the electrocoagulation forceps 223 contacts the human body, and the treatment apparatus for an endoscope, the human body tissue, the tissue operation apparatus, and the power supply form an electrical loop.

In this case, as shown in FIG. 30, the treatment apparatus for an endoscope is a monopolar apparatus, and the tissue operation apparatus is a monopolar apparatus. The first electrically conductive part is configured to contact a human body to form an electrical loop. The fourth electrically conductive part is grounded or connected to a passive power supply. The treatment apparatus for an endoscope, the human body tissue, the tissue operation apparatus, and the power supply form an electrical loop.

Embodiment 5

Differences between Embodiment 5 and Embodiment 1 are as follows:

The expandable frame 42 is silicone rubber that contains several conductive particles, and the conductive particles form the first electrically conductive part. That is, the expandable frame 42 is conductive. The expandable frame forms the first electrically conductive part 51 and the sliding contact part 53, and an additional first electrically conductive part 51 and sliding contact part 53 do not need to be provided.

Embodiment 6

Differences between Embodiment 6 and Embodiment 2 are as follows:

The expandable frame 42 is silicone rubber that contains several conductive particles, and the conductive particles form the first electrically conductive part. That is, the expandable frame 42 is conductive. The expandable frame forms the first electrically conductive part 51 and the sliding contact part 53, and an additional first electrically conductive part 51 and sliding contact part 53 do not need to be provided.

Embodiment 7

Differences between Embodiment 7 and Embodiment 3 are as follows:

The expandable frame 42 is silicone rubber that contains several conductive particles, and the conductive particles form the first electrically conductive part. The expandable frame 42 is conductive. The expandable frame forms the first electrically conductive part 51, and an additional first electrically conductive part does not need to be provided.

In the present invention, a space of contact between an outer side of the endoscope body of the endoscope and tissue is fully used to increase a conductive area of a contact part between the treatment apparatus for an endoscope and tissue in a return path, so that while the risk of bipolar instrument burns is reduced, a thermal effect between the high-frequency treatment part and tissue to be excised and electrocoagulated is further improved, thereby improving the security and operation efficiency of endoscopic surgery, and ensuring further clinical popularization and application of bipolar instruments.

The technical features in the foregoing embodiments may be randomly combined. For simplicity of description, all possible combinations of the technical features in the foregoing embodiments are not described. However, it should be considered that these combinations of technical features fall within the scope recorded in the specification provided that these combinations of technical features do not have any conflict.

The foregoing embodiments only describe several implementations of the present invention, and their description is specific and detailed, but cannot therefore be understood as a limitation to the patent scope of the present invention. It should be noted that a person of ordinary skill in the art may further make variations and improvements without departing from the conception of the present invention, and these all fall within the protection scope of the present invention. Therefore, the patent protection scope of the present invention should be subject to the appended claims.

What is claimed is:

1. A treatment apparatus for an endoscope, comprising:
a first electrode, comprising an electrical treatment part and an operating wire;
a second electrode, configured to be installed on the endoscope, the second electrode comprising a first electrically conductive part and a sliding contact part electrically connected to the first electrically conductive part, and the first electrically conductive part being configured to contact a human body;
a sheath, provided on a surface thereof with a second electrically conductive part, wherein
the operating wire is passed through the sheath, the sheath is configured to be passed through the endoscope, and when the sheath is located in a preset position, the sliding contact part contacts and is electrically connected to the second electrically conductive part and the sheath is in sliding fit with the sliding contact part;
the treatment apparatus further comprises an expandable frame, wherein the expandable frame is configured to be sleeved over the endoscope, the first electrically conductive part is provided outside the expandable frame, the first electrically conductive part is provided on the expandable frame.

2. The treatment apparatus for an endoscope according to claim 1, wherein a distance between a part, being configured to contact a human body, of the first electrically conductive part and an axis of the endoscope is greater than a radius of the endoscope.

3. The treatment apparatus for an endoscope according to claim 2, wherein a conductive material is provided on a peripheral surface of the expandable frame, and the conductive material forms the first electrically conductive part.

4. The treatment apparatus for an endoscope according to claim 2, wherein the expandable frame is silicone rubber that contains several conductive particles, and the conductive particles form the first electrically conductive part.

5. The treatment apparatus for an endoscope according to claim 2, wherein the expandable frame comprises a sleeve and a flexible part or an elastic part connected to the sleeve, the sleeve is configured to be sleeved over the endoscope, and the sliding contact part is fixed on an inner side of the sleeve.

6. The treatment apparatus for an endoscope according to claim 1, wherein the preset position is a particular range within which the sheath is slidable and the sliding contact part can contact and be electrically connected to the second electrically conductive part, a layer of a conductive material is provided on an outer surface of the sheath, and the conductive material forms the second electrically conductive part.

7. The treatment apparatus for an endoscope according to claim 1, wherein a first cavity and a second cavity are formed in the sheath, the operating wire is passed through the first cavity, a third electrically conductive part is provided in the second cavity, and the third electrically conductive part is electrically connected to the second electrically conductive part.

8. The treatment apparatus for an endoscope according to claim 1, wherein the second electrically conductive part surrounds the sheath by one loop in a circumferential direction of the sheath.

9. The treatment apparatus for an endoscope according to claim 1, wherein the sliding contact part comprises a fifth electrically conductive part and a sixth electrically conductive part, the sixth electrically conductive part is electrically connected to the first electrically conductive part, and the fifth electrically conductive part is electrically connected to the sixth electrically conductive part.

10. An expandable frame, wherein
the expandable frame is configured to be installed on an endoscope, a diameter of a peripheral surface of the expandable frame is greater than a diameter of a peripheral surface of the endoscope, a first electrically conductive part and a sliding contact part electrically connected to the first electrically conductive part are provided on the expandable frame, the first electrically conductive part is provided on a periphery of the expandable frame to contact human body tissue, and the sliding contact part contacts and is electrically connected to a second electrically conductive part of a treatment apparatus for the endoscope; the treatment apparatus comprising:
a first electrode, comprising an electrical treatment part and an operating wire;
a sheath, provided on a surface thereof with the second electrically conductive part, wherein
the operating wire is passed through the sheath, the sheath is configured to be passed through the endoscope, and when the sheath is located in a preset position, the sliding contact part contacts and is electrically connected to the second electrically conductive part and the sheath is in sliding fit with the sliding contact part.

11. The expandable frame according to claim 10, wherein the expandable frame comprises a sleeve and a transparent cover connected to the sleeve, the sleeve is configured to be sleeved over the endoscope, the transparent cover is transparent or translucent, and the transparent cover is configured to allow the endoscope to obtain an image.

12. The expandable frame according to claim 10, wherein the expandable frame comprises a sleeve and a flexible part or an elastic part connected to the sleeve, the sleeve is configured to be sleeved over the endoscope, and the sliding contact part is fixed on an inner side of the expandable frame.

13. The expandable frame according to claim 10, wherein a conductive material is provided on the peripheral surface of the expandable frame, and the conductive material forms the second electrically conductive part.

* * * * *